United States Patent [19]

Dattagupta

[11] Patent Number: 4,853,327

[45] Date of Patent: Aug. 1, 1989

[54] ENHANCED PHTHALAZINEDIONE CHEMILUMINESCENCE

[75] Inventor: Nanibhushan Dattagupta, New Haven, Conn.

[73] Assignee: Molecular Diagnostics, Inc., West Haven, Conn.

[21] Appl. No.: 753,739

[22] Filed: Jul. 10, 1985

[51] Int. Cl.$^4$ ...................... G01N 33/532; C12Q 1/68
[52] U.S. Cl. .......................................... 435/6; 435/7; 435/8; 435/28; 435/805; 435/809; 435/810; 362/24; 252/700
[58] Field of Search ...................... 435/6, 7, 8, 28, 805, 435/810, 809; 362/34; 252/700

[56] References Cited

U.S. PATENT DOCUMENTS

| | | | |
|---|---|---|---|
| 3,813,534 | 5/1974 | Gilliam | 362/34 |
| 3,819,925 | 6/1974 | Richter | 362/34 |
| 3,934,539 | 1/1976 | Little | 362/34 |
| 4,302,534 | 11/1981 | Halmann | 435/6 |
| 4,563,417 | 1/1986 | Albarella | 435/6 |
| 4,729,950 | 3/1988 | Kricka | 435/28 |

FOREIGN PATENT DOCUMENTS

| | | |
|---|---|---|
| 0070687 | 1/1983 | European Pat. Off. . |
| 0087959 | 9/1983 | European Pat. Off. . |
| 0103784 | 3/1984 | European Pat. Off. . |
| 0116454 | 8/1984 | European Pat. Off. . |
| 0219352 | 4/1987 | European Pat. Off. . |
| 8200479 | 1/1982 | Sweden . |

OTHER PUBLICATIONS

Schroeder, Analytical Chemistry, 48(13), p. 1933 (1976).

Campbell, Methods of Biochemical Analysis, 31, pp. 317, 318 and 394, 395 (1985).

Hackh's Chemical Dictionary, 3rd Edition, 1944, p. 43, McGraw-Hill Book Co.

Gary H. G. Thorpe, Robert Haggart, Larry J. Kricka and Thomas P. Whitehead, "Enhanced Luminescent Enzyme Immunoassays for Rubella Antibody, Immunoglobin and Digoxin", *Biochemical and Biophysical Research Communications,* vol. 119, No. 4, pp. 481–487, Mar. 15, 1984.

Thomas P. Whitehead, Gary H. G. Thorpe, Timothy J. N. Carter, Carol Groucutt and Larry J. Kricke, "Enhanced Luminescence Procedure for Sensitive Determination of Peroxidase-Labelled Conjugates in Immunoassay", *Nature,* vol. 305, pp. 158–159, Sep. 8, 1983.

*Photochemistry Photobiology,* vol. 40, pp. 823–830 (1984).

Irwin Fridovich, "The Stimulation of Horseradish Peroxidase by Nitrogenous Ligands", *The Journal of Biological Chemistry,* vol. 238, No. 12, Dec. 1963, pp. 3921–3927.

*Primary Examiner*—Robert J. Warden
*Assistant Examiner*—Robert Benson
*Attorney, Agent, or Firm*—Sprung Horn Kramer & Woods

[57] ABSTRACT

A chemiluminescence process comprising the contacting of a chemiluminescence precursor, an oxidant, an enzyme and a nitrogen compound selected from the group consisting of ammonia and a water-soluble organic amine. The reaction of such process can be used in detection of nucleic acid hybrids, antibodies, antigens and peroxidase enzymes and in producing light.

20 Claims, 1 Drawing Sheet

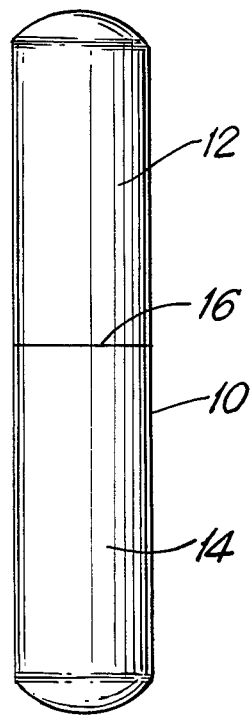

ENHANCED PHTHALAZINEDIONE CHEMILUMINESCENCE

BACKGROUND OF THE INVENTION

The present invention relates to chemiluminescent processes. The present invention relates more particularly to the detection of nucleic acid hybrids, antibodies, antigens and enzymes using chemiluminescence. Still further, the present invention concerns chemiluminescence devices.

Luminescence is defined as the emission of light without heat. In luminescence, energy is specifically channeled to a molecule so that a specific light-emitting state is produced without greatly increasing the temperature of the molecule. The color is determined by the character of the light-emitting state involved, and does not change when the energy or method to produce it is changed.

Chemiluminescence is defined as luminescence wherein a chemical reaction supplies the energy responsible for the emission of light (ultraviolet, visible, or infrared) in excess of that of a blackbody (thermal radiation) at the same temperature and within the same spectral range. Chemiluminescence thus involves the direct conversion of chemical energy to light energy. Below 500° C., the emission of any light during a chemical reaction involves chemiluminescence. The blue inner cone of a bunsen burner or the Coleman gas lamp are examples.

Many chemical reactions generate energy. Usually this exothermicity appears as heat, that is, translational, rotational, and vibrational energy of the product molecules; whereas, for a visible chemiluminescence to occur, one of the reaction products must be generated in an excited electronic state (designated below by an asterisk) from which it can undergo deactivation by emission of a photon. Hence a chemiluminescent reaction, as shown in reactions (a) and (b) below, can be regarded as the reverse of a photochemical reaction.

$$A + B \rightarrow C^* + D \tag{a}$$

$$C^* \rightarrow C + h\nu \tag{b}$$

The energy of the light quantum $h\nu$ (where h is Planck's constant, and $\nu$ is the light frequency) depends on the separation between the ground and the first excited electronic state of C; and the spectrum of the chemiluminescence usually matches the fluorescence spectrum of the emitter. Occasionally, the reaction involves an additional step, the transfer of electronic energy from C* to another molecule, not necessarily otherwise involved in the reaction. Sometimes no discrete excited state can be specified, in which case the chemiluminescence spectrum is a structureless continuum associated with the formation of a molecule, as in the so-called air afterglow: $NO + O \rightarrow NO_2 + h\nu$ (green light).

The efficiency of a chemiluminescence is expressed as its quantum yield $\phi$, that is, the number of photons emitted per reacted molecule. Many reactions have quantum yields much lower ($10^{-8}$ $h\nu$ per molecules) than the maximum of unity, Einsteins of visible light (1 einstein = $Nh\nu$, where N is Avogadro's number), with wavelengths from 400 to 700 nm, correspond to energies of about 70 to 40 kcal per mole (300 to 170 kilojoules per mole). Thus only very exothermic, or "exergonic," chemical processes can be expected to be chemiluminescent. Partly for this reason, most familiar examples of chemiluminescence involve oxygen and oxidation processes; the most efficient examples of these are the enzymes-mediated bioluminescences. The glow of phosphorus in air is a historically important case, although the mechanism of this complex reaction is not fully understood. The oxidation of many organic substances, such as aldehydes or alcohols, by oxygen, hydrogen peroxide, ozone, and so on, is chemiluminescent. The reaction of heated ether vapor with air results in a bluish "cold" flame, for example. The efficiency of some chemiluminescences in solution, such as the oxidation of luminol (I) (see formula below) and, especially, the reaction of some oxalate esters (II) (see formula below) with hydrogen peroxide, can be very high ($\phi = 30\%$).

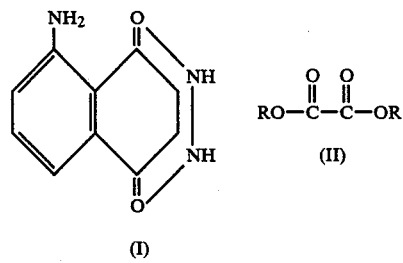

It is believed that the requirements for chemiluminescence are not only sufficient exothermicity and the presence of a suitable emitter, but also that the chemical process be very fast and involve few geometrical changes, in order to minimize energy dissipation through vibrations. For example, the transfer of one electron from a powerful oxidant to a reductant (often two radical ions of opposite charge generated electrochemically) is a type of process which can result, in some cases, in very effective generation of electronic excitation. An example, with 9,10-diphenylanthracene (DPA), shown in reaction (c).

$$DPA^- + DPA^+ \rightarrow DPA^* + DPA \tag{c}$$

The same is true of the decomposition of four-membered cyclic peroxides (III) into carbonyl products, shown in reaction (d), which may be the prototype of many chemiluminescences.

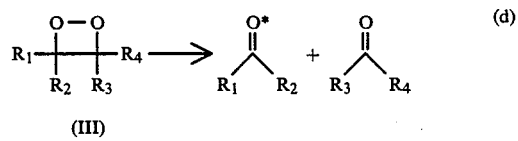

A special type of chemiluminescence is bioluminescence.

Bioluminescence is defined as the emission of light by living organisims, due to an energy-yielding chemical reaction in which a specific biochemical substance, called luciferin, undergoes oxidation, catalyzed by a specific enzyme called luciferase.

There are many specific luciferins and luciferases which are chemically different, each involved in some different living luminescent organism. The flash of the firefly, the brilliant "phosphorescence" or "burning" of the ocean, or the eerie glow of mushrooms deep in the forest at night are but a few examples of these different bioluminescent organisms.

Since bioluminescence is a type of chemiluminescence, it is not necessary to have a live organism to obtain light emission. The simple preservation of the chemicals involved will suffice. This can be done in some cases by rapidly drying the organism under mild conditions.

Dried firefly tails (lanterns) emit light when ground up with water. This light emission dies away within a few minutes, but can be restored by the addition of adenosinetriphosphate (ATP), a key coenzyme in the energy metabolism of cells. In this case, ATP reacts with the luciferin of fireflies to give the luciferyl adenylate intermediate and pyrophosphate (PP).

Using lantern extracts from hundreds of thousands of fireflies, scientists at Jophn Hopkins University determined the chemical structure of firefly luciferin to be $C_{13}H_{12}N_2O_3S_2$. It can now be synthesized. The reaction of luciferyl adenylate with oxygen is postulated to give a four-membered-ring alpha-peroxylactone intermediate and to release adenosinemonophosphate (AMP). This breaks down in the energy-yielding step to give carbon dioxide and a light-emitting excited molecule. This loses its energy as a photon (hν), in the yellow region of the spectrum in this case.

Firefly luciferin and luciferase from preserved light organs are used in a very sensitive biochemical test to detect AIP.

A postulated pathway for firefly luciferin is as follows:

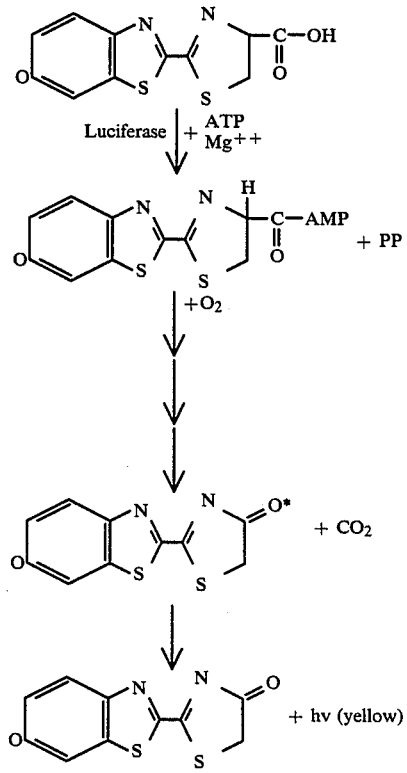

The luminescence of the firefly occurs as a brief flash, coming from the inside of photogenic cells in the lantern, under the control of the nervous system. Quite a different situation occurs in the small marine crustacean Cypidina, which is found in the waters off the coast of Japan. It synthesizes its luciferin and luciferase in separate glands. To emit light, it simply squirts luciferin and luciferase into the water, where the reaction occurs, separate from the animal. The light may function to divert or trick predators.

The chemistry of Cypridina luciferin has been determined by a group of chemists in Japan. $C_{22}H_{27}On_7$ is postulated to react directly wih oxygen as indicated below, forming a type of alpha-peroxylactone similar to the firefly molecule. In the final step, carbon dioxide is also released, along with the excited molecule, which in this case emits in the blue.

A postulated pathway for Cypridina luciferin is as follows:

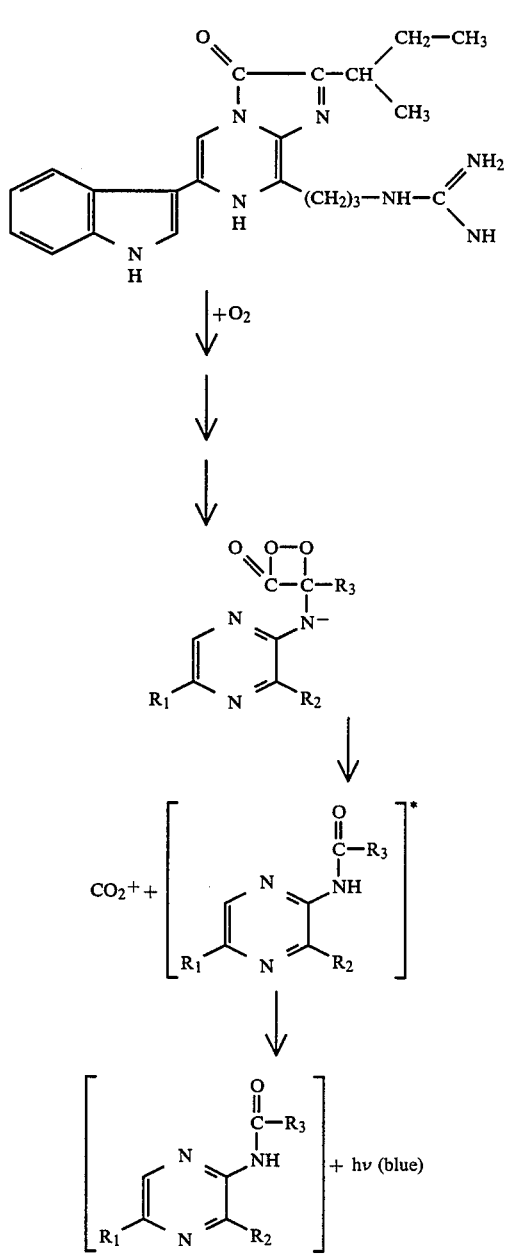

Like fireflies, dried Cypridina emit light when ground up with cool water; the preserved luciferin and luciferase are released from the glands as they are crushed. The light gradually fades as the luciferin is oxidized, but the addition of more luciferin restores light in the exhausted extract. Luciferin can be obtained either synthetically, or in the natural form by grinding up dried Cypridina in hot water. The heat destroys the luciferase, which is a protein, but leaves the luciferin active. When cooled and mixed with the exhausted extract, luminescence is observed. This is the basis for the classical luciferin-luciferase test.

Luminescent bacterial emit a continuous blue-green light. Such bacteria can be isolated directly from sea water or from the surface of a dead fish and will grow rapidly on any medium containing 3% salt (equivalent to sea water) and some fish or meat extract.

A postulated pathway for bacteria luciferin is as follows:

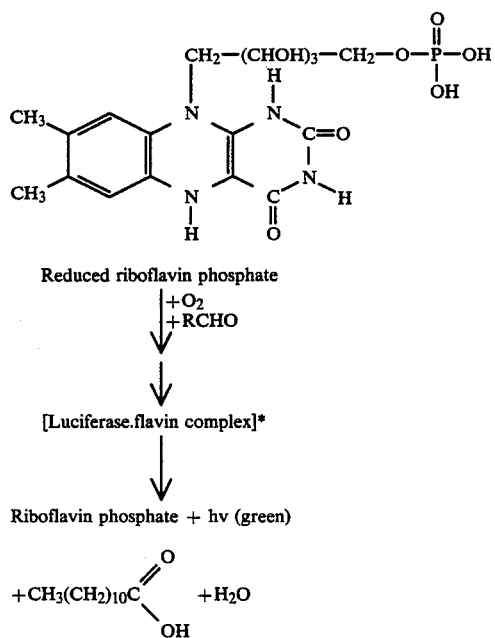

Reduced riboflavin phosphate $\downarrow +O_2$
$\downarrow +RCHO$

[Luciferase.flavin complex]*

$\downarrow$

Riboflavin phosphate + hv (green)

$+CH_3(CH_2)_{10}C\overset{O}{\underset{OH}{\diagup\!\!\!\diagdown}} \ +H_2O$

Chemiluminescent detection is one of the most sensitive ways of detecting an analyte. The process, although sensitive, suffers from several disadvantages. In most cases the chemiluminescent reaction mediated emission of light has a very short lifetime, i.e., light emission is very quick, so that a sophisticated device has to be developed to monitor the extent of light emission and also to determine the extent of the presence of an analyte. It is also difficult to couple the interacting systems to the analyte without destroying or changing the property of the interacting partners.

Recently, it has been demonstrated that if a substance, for example, an iodophenol or a benzothiazole derivative is present during the chemiluminescent emission mediated by horseradish peroxidase, the reaction rate is retarded and simultaneously the quantum yield of the light emission is enhanced (European patent application No. 0 116 454; European patent application No. 0 103 784; UK patent application No. 820 62 63; Gary H. G. Thorpe, Robert Haggart, Larry J. Kricka and Thomas P. Whitehead, "Enhanced Luminescent Enzyme Immunoassays for Rubella Antibody, Immunoglobulin And Digoxin", Biochemical and Biophysical Research Communications, Vol. 119, No. 2, pp. 481-487, Mar. 15, 1984; Thomas P. Whitehead, Gary H. G. Thorpe, Timothy J. N. Carter, Carol Groucutt and Larry J. Kricka, "Enhanced Luminescence Procedure For Sensitive Determination of Peroxidase-labelled Conjugates In Immunoassay", Nature, Vol. 305, pp. 158-159, Sept. 8, 1983; Gary H. G. Thorpe, Larry J. Kricka, Eileen Gillespie, Susan Mosely, Robert Amess, Neil Baggett and Thomas P. Whitehead, "Enhancement Of The Horseradish Peroxidase Catalysed Chemiluminescent Oxidation Of Cyclic Diacyl Hydrazides By 6-Hydroxybenzothiazoles", Anal. Biochem.). Although this method has been shown to be useful in the detection of an analyte by conventional immunoassay methods, it has never been demonstrated, however, whether this method could be utilized to detect a nucleic acid hybrid.

Irwin Fridovich, "The Stimulation Of Horseradish Peroxidase By Nitrogenous Ligands", The Journal of Biological Chemistry, Vol. 238, No. 12, December 1963, pp. 3921-3927, describes the stabilization of peroxidase in solution with nitrogenous ligands.

It has been demonstrated heretofore that a chemiluminescent reaction occurs where the emission is due to an iron initiated activation of bleomycin. The self-inactivation is affected by the presence of DNA.

In Photochemistry Photobiology, Vol. 40, pg 823-830, (1984), it was described that photoemission is quenched by target molecules such as DNA and that the presence of DNA does not prevent the iron-initiated activation of bleomycin, by the so-called self-inactivation reaction associated with chemiluminescence. The article went on to state that these findings seem to suggest that an electronically excited intermediate of bleomycin can alter bio-molecules though, in that case, the nature of the excited state was not precise.

Swedish patent application No. 8200479 describes chemiluminescent detection of nucleic acid hybrids.

European patent application No. 0 070 687 concerns a light-emitting polynucelotide hybridization diagnostic method.

Heretofore chemiluminescene reactions proceeded too quickly and thus resulted in light of only a short duration. The use of enhancers have somewhat extended and amplified the light from chemiluminescence reactions, however, the duration and intensity of the emitted light is still in many instances inadequate.

Immunoassy is one of the most widely used analytical techniques in the clinical laboratory. At present the majority of immunoassays employ a radioactive isotope, especially iodine-125, as a label. However, radioactive isotopes have a number of major disadvantages. First, the method of labelling involves the use of highly radioactive and hence potentially hazardous reagents. Second, the shelf life of the radio-actively labelled substance is often relatively short not only because by its very nature the radioactive isotope is continuously decaying but also because radioactively labelled proteins are often unstable. Third, it is often difficult to label proteins sufficiently to provide a sensitively and rapidly detectable reagent. Fourth, the disposal of radioactively labelled substances is inconvenient.

These disadvantages have stimulated a search for viable alternatives to the radio label. To be suitable as a label a substance should meet at least the following three requirements:

a. it should be detectable both rapidly and in very small quantities when attached to a ligand such as an antigen or an antibody;

b. it should be possible to attach it, without affecting its determination, to a ligand such as an antigen or an antibody; and c. once attached, it should not significantly alter the properties of the ligand.

Some of the most promising alternative labels are either substances which can themselves take part in a reaction resulting in the emission of luminescent light or substances which, on suitable treatment, produce compounds capable of taking part in a luminescent reaction. Heretofore, the use of luminescence in immunoassays has suffered since the measurement of luminescence is a rapid process and may be completed in a matter of seconds rather, than the several minutes generally required for the measurement of radioactivity.

Luminescence has been employed in three major luminescent or luminometric immunoassay systems:

a. Organoluminescent or organoluminometric immunoassays wherein chemiluminescent or bioluminescent compounds which participate directly in luminescent reactions (i.e., which are converted to an excited state and then return to a non-excited state with the emission of a photon) have been used to label ligands such as proteins, hormones, haptens, steroids, nucleic acids, metabolites, antigens and/or antibodies. Examples of suitable compounds include luminol and isoluminol;

b. Luminescent catalyst or cofactor immunoassays wherein catalysts or cofactors of luminescent reactions have been used as labels. An example of a suitable catalyst is the enzyme peroxidase; and c. Enzyme linked immunoassays wherein luminescent reactions have been used to determine the products formed by the action of enzyme labels on suitable substrates. An example of this type of immunoassay is the determination of antibody linked glucose oxidase by reacting the enzyme/antibody reagent with glucose to form hydrogen peroxide and then measuring the amount of hydrogen peroxide produced by adding luminol under controlled conditions to initiate a luminescent reaction.

The sensitivity of the above assays is determined in part by the lower limit for detection of the label or the product of the label. In the case of luminescent or luminometric assays the sensitivity of the system will depend partially on the light emitted in the luminescent reaction per unit of labelled material.

SUMMARY OF THE INVENTION

It is an object of the present invention to provide chemiluminescence reactions emitting light of long duration and high intensity.

It is also an object of the present invention to provide chemiluminescence devices capable of prolonged light duration.

It is a further object of the invention to detect nucleic acid hybrids.

It is still another object of the present invention to detect antibodies and antigens using chemiluminescence.

Another object of the present invention is the detection of enzyme in a sample.

These and other objects are realized by the present invention.

The present invention concerns a chemiluminescence process comprising the contacting of a chemiluminescence precursor, e.g., a 2-3-dihydro-1,4-phthalazinedione, an oxidant, e.g., hydrogen peroxide, an enzyme, e.g., a peroxidase enzyme, and a nitrogen compound selected from the group consisting of ammonia and a water-soluble organic amine.

The present invention also concerns a chemiluminescence device comprising a vessel and a means for combining a chemiluminescence precursor, an oxidant, an enzyme and a nitrogen compound selected from the group consisting of ammonia and a water-soluble organic amine.

The present invention relates to an enhanced and delayed chemiluminescent assay particularly useful for clinical diagnosis of certain kinds of disease states which can be monitored by immunological reactions or by nucleic acid hybridization method. The invention can also be utilized for straightforward sample analysis where one of the reacting components for the assay is already present in the test sample in an unknown amount. The diagnosis of disease states by using immunoassay and also by nucleic acid hybridization assays require highly sensitive detection systems. Since the amount of analyte present is usually very little, the assay condition should provide enough amplified detection. For example, in the detection of an infectious agent such as a microorganism in a blood sample, it is possible to extract DNA from the blood sample which is already infected by the microorganisms and use a nucleic aid probe specific for that microorganism. The detection can be conducted by hybridization with the DNA extracted from the test blood sample and the nucleic acid probe specific for the microorganism which presumably has infected the blood sample.

Nucleic acid hybridization technology can also be used for the detection of genetic diseases which are not manifested through an infectious agent, for example, a point mutation on the beta-hemoglobin gene gives rise to a defect known as sickle cell anemia. People who affected with some mutation and also who are carriers of such defects have a specific sequence of nucleic acid in their genome which can be detected by hybridization technology. For the detection of a single gene point mutation it is essential that a highly sensitive technique is available because of the low concentration of the defective gene. Usually the radioactively labeled isotopes are used for the detection process. The present invention provides a highly sensitive chemiluminescence assay which is mediated by a peroxidase-like enzyme and a diacylhydrazide-like substrate for light substrate for light emission in the presence of a peroxide. Among the other assays where the present invention is useful includes the assay of elastin or the assay of glucose by using glucose oxidase peroxidase system. The principle and the utility of these assays are known in the art and have discussed hereinabove, wherein it was demonstrated that a chemiluminescence type assays can be used for the detection of elastin or glucose and that chemiluminescent type assay can be used for immunoassay purposes. The present invention is based on a surprising observation that certain nitrogenous materials slow down the rate of emission of light and prolong the activity of the enzyme for a long period of time in a chemiluminescence reaction. From the combination of these two effects it can be concluded that the nitrogeneous materials enhance and delays the chemiluminescence emission from diacylhydrazides mediated by peroxidase and hydrogen peroxide.

The present invention also concerns processes for detecting a nucleic acid hybrid.

In one process according to the present invention for detecting a nucleic acid hybrid an unknown DNA containing sample is contacted in a mixture, for example, a solution, with a probe comprising contacting a defined nucleic acid sequence linked, e.g., photochemically linked, such as by the use of furocourmarin, to a chemiluminescence precursor, the mixture containing an oxidant, an enzyme and a nitrogen compound selected from the group consisting of ammonia and a water-soluble organic amine, and then determining the extent of light emission.

In another process according to the present invention for detecting a nucleic acid hybrid, an unknown DNA-containing sample is contacted in a mixture, for example, a solution, with a probe comprising contacting a defined nucleic acid sequence and an enzyme linked to the nucleic acid sequence, the mixture containing a chemiluminescence precursor, an oxidant and a nitrogen compound selected from the group consisting of ammonia and a water-soluble organic amine and then determining the extent of light emission.

The present invention also concerns chemiluminescence assays.

A chemiluminescence immunoassay for the detection of an antibody in an unknown sample according to the present invention comprises contacting the sample with an antigen linked to a chemiluminescene precursor or an enzyme, contacting the sample and the antigen with an oxidant, a nitrogen compound selected from the group consisting of ammonia and a water-soluble organic amine and an enzyme if the antigen is linked to a chemiluminescence precursor, or a chemiluminescence precursor if the antigen is linked to an enzyme, and determining the extent of light emission.

A chemiluminescence immunoassay for the detection of an antigen in an unknown sample according to the present invention comprises contacting the sample with an antibody to the antigen, the antibody linked to a chemiluminescence precursor or an enzyme, contacting the sample and said antibody with an oxidant, a nitrogen compound selected from the group consisting of ammonia and a water-soluble organic amine and an enzyme of the anitgen is linked to a chemiluminescence precursor, or a chemiluminescence precursor if the antigen is linked to an enzyme, and determining the extent of light emission.

The present invention further concerns a chemiluminescence assay for the detection of a peroxidase enzyme comprising contacting an unknown sample with a chemiluminescence precursor, an oxidant and a nitrogen compound selected from the group consisting of ammonia and a water-soluble organic amine and determining the extent of light emission.

Still further, the present invention involves a test kit for conducting chemiluminescence assays comprising a chemiluminescence precursor, an enzyme, an oxidant and a nitrogen compound selected from the group consisting of ammonia and a water-soluble organic amine.

The present invention also relates to a chemiluminescence device composed of a vessel containing a nitrogen compound selected from the group consisting of ammonia and a water-soluble organic amine and chemiluminescence reactants, i.e., a chemiluminescence precursor, an oxidant and an enzyme. In an embodiment of such device, the vessel contains at least two compartments with each of two compartments containing at least one, but not all of the chemiluminescence reactants, and means for allowing the controlled flow of the nitrogen compound and reactants from one compartment to the other.

BRIEF DESCRIPTION OF THE DRAWING

The FIGURE is an elevational view of a chemiluminescence device according to the present invention.

DETAILED DESCRIPTION OF THE INVENTION

Non-limiting examples of nitrogen compounds for use in the present invention include ammonia and its salts, heterocyclic aromatics and water-soluble amines. Exemplary of salts of ammonia for use in the present invention are, for example, acetate, chloride, nitrate sulfate, phosphate and borate salts, primary, secondary, tertiary and quaternary ammonium salts where the protons are exchanged with alkyl or aryl residues. Non-limiting examples of heterocyclic nitrogen compounds for use in the present invention include imidazoles and their alkyl derivatives and pyridine and alkyl derivatives thereof. Amines for use in the present invention include alkyl amines, polyamines, aryl amines e.g benzylamines. Non-limiting examples of polyamines for employment in the present invention include putrescine (butylene-diamine), spermine, spermidine, and their alkyl salts. Thiazines can also be used.

Alkylamines for use in the present invention are exemplified by the formula

where $X_1$, $X_2$ and $X_3$ are the same or different and are aliphatic saturated hydrocarbon radicals. Non-limiting examples of aliphatic saturated hydrocarbon radicals for use in the present invention include unsubstituted and substituted alkanes having 1 to 8 carbon atoms, preferably 1 to 8 carbon atoms. Non-limiting examples of substituents for such substituted alkanes include hydroxy, nitro, halo (e.g., fluoro, chloro, bromo, iodo), carboxy, amide and the like.

Chemiluminescence precursors for use in the present invention include 2,3-dihydro-1,4-phthalazinediones ("DPD"). Preferably the 2,3-dihydro-1,4-phthalazinediones is of the formula

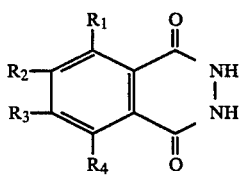

wherein $R_1$ is amino and each of $R_2$, $R_3$ and $R_4$ is H, optionally substituted $C_1$-$C_6$-alkyl or alkenyl, hydroxyl, $C_1$-$C_6$-alkoxy, carboxyl, amino or $R_2$ is amino and each of $R_1$, $R_3$ and $R_4$ is H, unsubstituted or substituted $C_1$-$C_6$-alkyl or alkenyl, hydroxyl, $C_1$-$C_6$-alkoxy, carboxyl or amino, or $R_1$ and $R_2$ are together and are an amino or substituted amino derivative of a benzo-group, and each of $R_3$ and $R_4$ is H, optionally substituted $C_1$-$C_6$-alkyl or alkenyl, hydroxyl, $C_1$-$C_6$-alkoxy, carboxyl, or amino. Particularly preferred chemiluminescene precursors are 5-amino-2,3-dihydro-1,4-phthalazinedione (luminol) and 6-amino-2,3-dihydro-1,4-phthalazinedione (isoluminol).

Substituted alkyl, alkenyl and amine radicals for use in the present invention are well known in the art. Non-limiting examples of substituents for such substituted radicals include halogen, e.g., chloro-, fluoro-, bromo-, and iodo-, hydroxy, carboxy, nitro, cyano and thiol. Furthermore, amine radicals for use in the present invention can be substituted by alkyl, preferably having 1 to 10 carbon atoms, and alkenyl, preferably having 2 to 10 carbon atoms. Hydroxyl radicals for use in the present invention can be substituted by halogen, alkyl, preferably having 1 to 10 carbon atoms, or alkenyl, preferably having 2 to 10 carbon atoms.

Generally any peroxidase enzyme can be used in the present invention. Non-limiting examples of enzymes for use in the present invention include horseradish peroxidase (HRP), microperoxidase and lactoperoxidase.

Any oxidant which reacts with the chemiluminescene precursor to cause excitation of the chemiluminescence precursor so that it emits light in a luminescent reaction, may be employed in the present invention. Particularly preferred oxidants are hydrogen peroxide, perborate ion and sodium peroxidate.

An example of a buffered amine for use in the present invention is ammonia.

Secondary reaction factors include temperature, pH, reagent concentration, mixing speed and method of light measurement. To maximize the sensitivity of the present system these secondary factors should be adjusted to obtain the maximum light emission, in a reproducible and easily measurable manner, with the signal to background ratio as high as possible.

The conditions chosen generally involve a compromise involving the enzyme or catalytic activity of the oxidant, the kinetics of the reaction, the apparatus employed, the signal to background ratio and the sensitivity required.

In order to achieve optimum results the present chemiluminescent reactions should be conducted under moderate conditions of temperature ranging from 10° C. to 50° C., and pH, in the range of 6 to 10, preferably between 7 and 9. The luminescence of the process of the present invention is not limited to these temperature ranges and tenperature is not per se critical. Suitable buffering substances that can be employed in the present invention are phosphate, tris (hydroxmethyl) aminoethane, 2-amino-2-methyl-1,3-propanediol, acetate, carbonate and borate.

The following reagent concentrations (when added to a solution) are particularly suitable for use in the present invention:

| | |
|---|---|
| enzyme | .01 ng to 5000 mg/liter |
| oxidant | 10 μmol to 300 mmol/liter |
| chemiluminescent substance | 0.5 μmol to 200 mmol/liter |
| nitrogen compound | 5 μmol to 500 mmol/liter |

One aspect of the present invention involves the detection of nucleic acid hybrids.

One nucleic acid probe for use in the process of the present invention comprises a nucleic acid sequence bound to a ligand, such ligand bound to a binding protein and such binding protein bound to an enzyme. The nucleic acid sequence can be bound to the ligand by an intercalator compound such as a furocourmarin or a phenanthridine compound, or by a non-intercalator compound such as netropsin, distamycin and bis-benzimidazole. Particularly preferred intercalator compounds are fuorocourmarins, for example, angelicin (isopsoralen), psoralen and derivatives thereof, e.g., 4-aminomethyl-4-5'-dimethyl angelicin, 4'-aminomethyltrioxsalen, 3-carboxy-5- or -8-amino- or -hydroxy-psoralen, as well as mono- or bis-azido aminoalkyl methidium or ethidium compounds.

Non-limiting examples of intercalating agents for use in the present invention are exemplified in the following Table:

TABLE

| Intercalator Classes and Representative Compounds | Literature References |
|---|---|
| A. Acridine dyes | J. Lerman, Mol. Biol., 3, 18 (1961); Bloomfield et al, Physical Chemistry of Nucleic Acids, Chapter 7, pp. 429-476, Harper and Rowe, NY (1974); |
| proflavin, acridine orange, quinacrine, acriflavine | Miller et al, Biopolymers, 19, 2091 (1980) |
| B. Phenanthridines | Bloomfield et al, supra |
| | Miller et al, supra |
| ethidium | |
| coralyne | Wilson et al, J. Med. Chem., 19, 1261 (1976) |
| ellipticine, ellipticine cation and derivatives | Festy et al, FEBS Letters, 17, 321 (1971); Kohn et al, Cancer Res., 35, 71 (1976); LePecq et al, PNAS (USA), 71, 5078 (1974); Pelaprat et al, J. Med. Chem., 23, 1330 (1980) |
| C. Phenazines | Bloomfield et al, supra |
| 5-methylphenazine cation | |
| D. Phenothiazines | ibid |
| chlopromazine | |
| E. Quinolines | ibid |
| chloroquine | |
| quinine | |
| F. Aflatoxin | ibid |
| G. Polycyclic hydrocarbons and their oxirane derivatives | ibid |
| 3,4-benzpyrene benzopyrene diol epoxide, 1-pyrenyl-oxirane | Yang et al, Biochem. Biophys. Res. Comm, 82, 929 (1978) |
| benzanthracene-5,6-oxide | Amea et al, Science, 176, 47 (1972) |
| H. Actinomycins | Bloomfield et al, supra |
| actinomycin D | |
| I. Anthracyclinones | ibid |
| beta-rhodomycin A | |
| daunamycin | |
| J. Thiaxanthenones | ibid |
| miracil D | |
| K. Anthramycin | ibid |
| L. Mitomycin | Ogawa et al, Nucl. Acids Res., Spec. Publ. 3, 79 (1977); Akhtar et al, Can. J. Chem., 53, 2891 (1975) |
| M. Platinium Complexes | Lippard, Accts. Chem. Res., 11, 211 (1978) |
| N. Polyintercalators | |
| echinomycin | Waring et al, Nature, 252, 653 (1974); Wakelin, Biochem. J., 157, 721 (1976) |
| quinomycin triostin BBM928A | Lee et al, Biochem. J., 173, 115 (1978); Huang et al, Biochem, 19, 5537 (1980); |
| tandem | Viswamitra et al, Nature, 289, 817 (1981) |
| diacridines | LePecq et al, PNAS (USA), 72, 2915 (1975); Carrellakis et al, Biochem. Biophys. Acta, 418, 277 (1976); Wakelin et al, Biochem, 17, 5057 (1978); Wakelin et al, FEBS Lett., 104, 261 (1979); Capelle et al, Biochem., 18, 3354 (1979); |

TABLE-continued

| Intercalator Classes and Representative Compounds | Literature References |
|---|---|
| ethidium dimer | Wright et al, Biochem., 19, 5825 (1980); Bernier et al, Biochem. J., 199, 479 (1981); King et al, Brochem., 21, 4982 (1982) Gaugain et al, Biochem., 17, 5078 (1978); Kuhlman et al, Nucl. Acids Res. 5, 2629 (1978); Marlcovits et al, Anal. Biochem., 94, 259 (1979); Dervan et al, JACS, 100, 1968 (1978); ibid 101, 3664 (1979) |
| ellipticene dimers and analogs | Debarre et al, Compt. Rend. Ser. D., 284, 81 (1977); Pelaprat et al, J. Med. Chem., 23, 1336 (1980) |
| heterodimers | Cain et al, J. Med. Chem., 21, 658 (1978); Gaugain et al, Biochem., 17, 5078 (1978) |
| trimers | Hansen et al, JCS Chem. Comm., 162 (1983); Atnell et al, JACS, 105, 2913 (1983) |
| Norphillin A | Loun et al, JACS, 104, 3213 (1982) |
| P. Fluorenes and fluorenones | Bloomfield et al, supra |
| fluorenodiamines | Witkowski et al, Wiss. Beitr.-Martin-Luther-Univ. Halee Wittenberg, 11 (1981) |
| Q. Furocoumarins angelicin | Venema et al, MGG, Mol. Gen. Genet., 179, 1 (1980) |
| 4,5′-dimethylangelicin | Vedaldi et al, Chem.-Biol. Interact, 36, 275 (1981) |
| psoralen | Marciani et al, Z. Naturforsch B, 27(2), 196 (1972) |
| 8-methoxypsoralen | Belognzov et al, Mutat. Res., 84, 11 (1981); Scott et al, Photochem. Photobiol., 34, 63 (1981) |
| 5-aminomethyl-8-methoxypsoralen | Hansen et al, Tet. lett., 22, 1847 (1981) |
| 4,5,8-trimethyl-psoralen | Ben-Hur et al, Biochem. Biophys, Acta, 331, 181 (1973) |
| 4′-aminomethyl-4,5,8-trimethylpsoralen | Issacs et al, Biochem, 16, 1058 (1977) |
| xanthotoxin | Hradecma et al, Acta Virol., (Engl. Ed.) 26, 305 (1982) |
| khellin | Beaumont et al, Biochem. Biophys. Acta, 608, 1829 (1980) |
| R. Benzodipyrones | Murx et al, J. Het. Chem., 12, 417 (1975); Horter et al, Photochem. Photobiol., 20, 407 (1974) |
| S. Monstral Fast Blue | Jurarranz et al, Acta Histochem., 70, 130 (1982) |

Particularly useful intercalating agents are the azidointercalators. Their reactive nitrenes are readily generated at long wavelength ultraviolet or visible light and the nitrenes of arylazides prefer insertion reactions over their rearrangement products (White et al, *Methods in Enzymol.*, 47, 644 (1977)). Representative azidointercalators are 3-azidoacridine, 9-azidoacridine, ethidium monoazide, ethidium diazide, ethidium dimer azide (Mitchell et al, *JACS*, 104, 4265 (1982)), 4-azido-7-chloroquinoline, and 2-azidofluorene. Other useful intercalators are the furocoumarins which form [2+2] cycloadducts with pyrimidine residues. Alkylating agents can also be used such as bischloroethylamines and epoxides or aziridines, e.g., aflatoxins, polycyclic hydrocarbon epoxides, mitomycin, and norphillin A.

Suitable angelicin derivatives for use in the present invention have the following formula

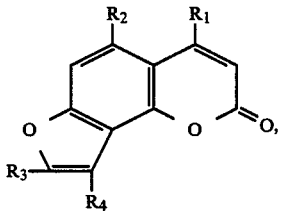

wherein $R_1$, $R_2$, $R_3$ and $R_4$ are as follows:

| $R_1$ | $R_2$ | $R_3$ | $R_4$ |
|---|---|---|---|
| H | H | H | H |
| $CH_3$ | H | $CH_3$ | H |
| $CH_3$ | $CH_3$ | $CH_3$ | $CH_2OH$ |
| $CH_3$ | H | $CH_3$ | $CH_2OCH_3$ |
| $CH_3$ | H | $CH_3$ | $CH_2NH_2$ |
| $CH_3$ | H | $CH_3$ | $CH_2Cl$ |
| $CH_3$ | H | $CH_3$ | 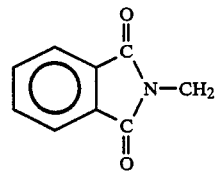 |

Many other compounds with different R's can be synthesized following published procedures.

Suitable psoralen derivatives for use in the present invention have the formula

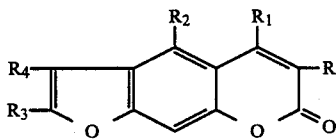

in which
R, $R_1$ and $R_3$ each independently is hydrogen or lower alkyl,
$R_4$ is hydrogen, lower alkyl or lower alkyl substituted by hydroxy, lower alkoxy, amino, halo and/or

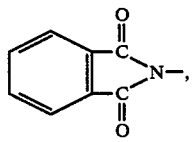

and $R_2$ and $R_5$ each independently is hydrogen, hydroxy, carboxy, carbo-lower alkoxy or lower alkoxy.

Angelicin derivatives are superior to psoralen compounds for monoadduct formation. If a single-stranded probe is covalently attached to some extra double-stranded DNA, use of phenanthridum and psoralen compounds is desirable since these compounds interact preferentially to double-stranded DNA in the dark.

Non-limiting examples of nucleic acid sequences for use in the present invention can be singly or doubly stranded DNA or RNA or fragments thereof, such as are produced by restriction enzymes or even relatively short oligomers.

In a embodiment of the present invention the probe is immobilized on a solid support, for example, nitrocellulose paper.

Probes And Formats For Hybridization

There are different types of probes and formats which can be used for hybridization assays and detection by following the method of the present invention.

Essentially any nucleic acid hybridization format can be followed for the purposes of the present invention in which either the hybrids formed between the probe and the sequence to be determined or the probe which has not hybridized with the sequence of interest are labelable with the selected chemiluminescence label. As is known in the art, the labeling of such hybrids or unhybridized probe can be accomplished before or after the actual hybridization reaction. Normally, the probe is either labelled or labelable through a specific bridging reaction or the formed hybrids are subsequently labeled, usually through a specific bridging reaction. A central novel feature of the present invention is the advantageous application of the phenomenon of enhanced chemiluminescence to the detection of nucleic acid hybridization.

The probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'-5'-terminii by nonhomologous sequences, such as those comprising the DNA or RNA of a vector into which the homologous sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Particularly preferred will be linear or circular probes wherein the homologous probe sequence is in essentially only single stranded form (see particularly, Hu and Messing, *Gene,* 17, 271–277 (1982)).

The formats where a single polynucleotide sequence is used as a probe is common in the prior art. The probe can be labeled in such a way that will be able to participate in the chemiluminescence reaction. This can be achieved by labeling the probe with a ligand as, for example, biotin which specifically binds to a protein and that protein can be a carrier for the chemiluminescent reaction component, as for example linked covalently to luminol or horseradish peroxidase.

The probe can also be directly linked to the chemiluminescent reaction partners. The probe can be photochemically linked to luminol or horseradish peroxidase. The probe can also be produced in such a fashion that after the hybridization the hybrid will behave immunologically distinct from the rest of the reaction components, for example, if a DNA probe is used for the detection of RNA or an RNA probe is used for the detection of DNA, the DNA/RNA hybrid produces immunologically specific antibodies which will recognize those hybrids and those specific recognition can be utilized for the detection of the hybrid. If the RNA probe is immobilized, the hybrid is likewise immobilized and an antibody specific for the RNA/DNA hybrid is reacted with the hybrid. If the antibody carries a label which can participate in the chemiluminescent reaction, the hybrid can be detected via the antibody, and the chemiluminescent process. As, for example, of the RNA/DNA hybrid specific antibody is covalently linked to horseradish peroxidase after the hybridization and interaction with the peroxidase-linked antibody it should be possible to initiate chemiluminescent reaction by adding the precursor and an oxidant.

There are several other ways a nucleic acid can be made immunogenic and immunologically distinct from the other nucleic acids. Antibodies which are selective for RNA/RNA or DNA/DNA hybrids are also known and can be similarly used. In addition, if a nucleic acid interacts with an intercalator, the nucleic acid complex becomes immunologically distinct from the unreacted nucleic acid. In a hybridization format if a probe is prepared such that the probe will provide such interaction sites after the hybridization, an antibody assay can be conducted for the detection of the hybrid.

Practice of the analytical methods of the present invention is not limited to any particular hybridization format. Any conventional hybridization technique can be used. As improvements are made and as conceptually new formats are developed, such can be readily applied to carrying out the present method. Conventional hybridization forms which are particularly useful include those wherein the sample nucleotide acids or the polynucleotide probe is immobilized on a solid support (solid-phase hybridization) and those wherein the polynucleotide species are all in solution (solution hybridization).

Solid-Phase Hybridization Formats

In solid-phase hybridization formats, one of the polynucleotide species participating in hybrization is fixed in an appropiate manner in its single stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected by the methods as described herein.

Normally, the probe is labeled directly or indirectly through one or more specific binding pairs with the selected chemiluminescence label. As used herein, indirect labeling, immobilization, or other modification through one or more specific binding pairs intends the coupling of one of a pair mutually binding substances to the material to be labeled, etc., e.g., probe, and the labeling, immobilization, etc. of the other member of the pair. Useful binding parts include biotin/avidin (including egg white aviden and streptavidin), haptens and antigens/antibodies, carbohydrates/lectins, enzymes/inhibitors, and the like as are known in the art. One can also use bridging pairs, such as coupling biotin or a hapten to the material to be labeled, etc., and also to the label, solid-phase, etc., and using avidin or an antihapten, respectively, to bridge the two.

When using labeled probe and immobilized sample nucleic acids, the resulting hybrids are separated from the unhybridized probe, and the chemiluminescence reaction is initiated in one or the other of the separate fractions. Alternatively, the hybrids and unhybridized probe do not have to be separated if hybrids are detected by anti-hybrid antibodies which distinguish the hybrids from the unhybridized single stranded probe. Such antibodies can be selective for mixed DNA/RNA hybrids or selective on RNA/RNA or DNA/DNA hybrids, or can be selective for intercalator duplexes where an intercalating agent has been introduced to the hybrids. Such antibody reagents will be describe in more detail below.

An alternative method to those involving sample nucleic acid immobilization uses immobilized probe and detection of resulting immobilized hybrids with an anti-hybrid antibody labeled directly or through specific binding pairs with the selected chemiluminescence label as described above. When presented to the hybridization reaction in an immobilized form, the probe can be in any appropriate form that enables the probe, and any components of the reaction mixture that have become associated therewith by hybridization and/or by binding of the anti-hybrid reagent, to be subsequently isolated or separated from the remaining mixture such as by centrifugation, filtration, chromatography, or decanting. A variety of compositions and configurations of an immobilized probe will thus be evident and available to the worker in the field. Essentially any form of the probe that is insoluble in the reaction mixture can be used. For example, the probe can be aggregated or otherwise precipitated, attached to an insoluble material, polymer, or support, or entrapped in a gel such as agarose or polyacrylamide (see *Meth. Enzymol.,* 12B:635 (1968) and PNAS, 67, 807 (1970)). It is particularly preferred to employ a solid support to which the probe is attached or fixed by covalent or noncovalent bonds, the latter including adsorption methods that provide for a suitably stable and strong attachment. The solid support can take on a variety of shapes and compositions, including microparticles, beads, porous and impermeable strips and membranes, the interior surface of reaction vessels such as test tubes and microtiter plates, and the like. Means for attaching a desired reaction partner to a selected solid support will be a matter of routine skill to the worker in the field.

One method for adsorbing the probe onto nitrocellulose membranes involves saturating a solution of probe with sodium iodide and spotting or filtering aliquots onto the membrane (Bresser et al, *DNA,* 2, 243 (1983)). The sodium iodide facilitates denaturation of the probe and enhances adsorption onto the membrane. Alternatively, the probe can be treated with glyoxal, usually at concentrations around 1 molar(M), and then adsorbed onto the membrane. The probe is fixed by baking at around 80° C. undervacuum for a period in the range of 2-4 hours. (P. S. Thomas, *Meth. In. Enzymol.,* 100, 255 (1983)).

Covalent immobilization of RNA or DNA probes can also be accomplished. A wide variety of support materials and coupling techniques can be employed. For example, the probe can be coupled to phosphocellulose through phosphate groups activated by carbodiimide or carbonyldiimidazole (E. K. F. Bautz, and B. D. Hall, *Proc. Nat'l. Acad. Sci. USA,* 48, 400–408 (1962); T. Y. Shih and M. A. Martin, *Biochem,* 13, 3411–3418 (1974). Also, diazo groups on m-diazobenzoyloxymethyl cellulose can react with guanine and thymidine residues of the polynucleotide (B. E. Noyes and G. R. Stark, *Cell,* 5, 301–310 (1975); J. Reiser et al, *Biochem. Biophys. Res. Commun.,* 85, 1104–1112 (1978)). Polysaccharide supports can also be used with coupling through phosphodiester links formed between the terminal phosphate of the polynucleotide and the support hydroxyls by water soluble carbodiimide activation (D. Richwood, *Biochim. Biophys. Acta,* 269, 47–50 (1972); P. T. Gilham, *Biochem,* 7, 2809–2813 (1968)), or by coupling nucleophilic sites on the polynucleotide with a cyanogen bromide activated support (D. J. Arndt-Jovin et al., *Eur. J. Biochem.,* 54, 411–418 (1975); U. Linberg and S. Ericksson, *Eur. J. Biochem.,* 18, 474–479 (1971)). Further, the 3'-hydroxy terminus of the probe can be oxidized by periodate and coupled by Schiff base formation with supports bearing amine or hydrazide groups (P. T. Gilham, *Method. Enzymol.,* 21, 191–197 (1971); H. D. Hansske et al, *Method. Enzymol.,* 59, 172–181 (1979)). Supports having nucleophilic sites can be reacted with cyanuric chloride and then with the polynucleotide (H. D. Hunger et al, *Biochim. Biophys. Acta,* 653, 344–349 (1981)).

In general, any method can be employed for immobilizing the probe, provided that the complementary single stranded sequence is available for hybridization to sample nucleic acids. Particular methods or materials are not critical to the present invention.

Another method of interest is the sandwich hybridization technique wherein one of two mutually exclusive fragments of the homologous sequence of the probe is immobilized and the other is labeled. The presence of the polynucleotide of interest results in dual hybridization to the immobilized and labeled probe segments, again with the same ultimate measurement results in dual hybrization to the immobilized and labeled probe segments, again with the same ultimate measurement of support-associated labeled hybrids. See *Methods in Enzymology,* 65, 468 (1980) and *Gene,* 21, 77–85 (1983) for further details.

For purposes of better illustration, the following solid-phase hybridization methods involving detection with antibody to intercalated duplexes are particularly useful in the present invention.

In a first method, the single stranded nucleic acids from the liquid test medium are first immobilized on a solid support. A hybridization reaction mixture is then formed by contacting the immobilized sample nucleic acids with the probe which in this case comprises, in addition to the complementary single stranded portion, at least one double stranded portion which is chemically linked with the intercalator in the form of intercalation complexes. A particularly useful form of the probe is the circular form described by Hu and Messing, supra. The resulting hybridization aggregate comprises the immobilized polynucleotide of interest hybridized with the probe which has a covalently linked, intercalated double stranded region. The solid support carrying immobilized duplexes is then preferentially separated from the remainder of the reaction mixture. The antibody is added, preferably labeled with the selected chemiluminescence label, and the resulting immobilized antibody bound to intercalation complexes in the aggregate is separated from the remainder of the reaction mixture. The antibody bound to the support is then determined to complete the assay. Alternatively, the antibody in the separated solution can be determined; although this will generally be less preferred since a large excess of antibody is normally used.

A variation of this method is to employ a probe such as above, but not having covalently linked intercalator bound to the double stranded region. Rather, the intercalator is added to the immobilized aggregate resulting in the formation of intercalator complexes in both the double stranded portion of the probe and the duplexed region formed by hybridization.

A second method is based on a sandwich format where a reaction mixture is formed among the test medium containing the sequence of interest and the first and second probes, each comprising respectively at least one base sequence complementary to a mutually exclusive portion of the sequence of interest. The first probe is immobilized on a solid support and the second probe is modified with covalently linked, intercalation complexes as in the previous method. The resulting hybridization aggregate comprises the sequence of interest hybridized to both the immobilized first probe and the intercalation complex-modified second probe. The antibody is added, preferably in labeled form, and the resulting immobilized antibody bound to intercalation complexes in the aggregate is separated from the remainder of the reaction mixture. The bound antibody is determined to then complete the assay.

There are several useful variations of this second method. First, as in the case of the variation of the first method, one can employ a probe which does not comprise covalently linked intercalator, but rather can add free intercalator to the immobilized aggregate, resulting in the formation of intercalator complexes with all available double stranded regions. Also, as an alternative to using a second probe with a double stranded portion, one can use a probe of entirely single stranded nucleic acid with intercalator chemically linked thereto so that upon hybridization there are formed intercalation complexes, or with intercalator being added so that intercalation occurs between the duplexes formed between the two probes and the sequence to be detected.

In a third method, the sample nucleic acids are contacted with immobilized probe and preferably the resulting immobilized duplexes are separated from the remainder of the reaction mixture. In this format, the probe is in single stranded form. The resulting hybridization product comprises the immobilized probe hybridized with the sequence of interest. Also, this format allows significant reannealing between complementary regions of sample nucleic acid which can take place on the immobilized aggregate. Such reannealing works to the advantage of the assay since it provides additional double stranded nucleic acid for subsequent intercalation. The next step in the assay is to add intercalator and the antibody, again preferably in a labeled form. The assay is completed by separation and antibody determination steps as in the previous formats.

Finally, there is a fourth method wherein the single stranded sample nucleic acids are contacted with immobilized probe where, in this case, such probe is chemically, e.g., covalently, to the intercalator such that duplex formation in the region of the linked intercalator results in formation of intercalation complexes. This is a highly advantageous format in that the probe is both immobilized and modified, requiring no immobilization or modification step to be performed at the time of the assay. The resulting aggregate comprises covalently linked, intercalation complexes in the region of hybridization between sample and probe nucleic acids and in any reannealed sample regions. Antibody is then added and the assay completed as in the previous formats. This format provides the advantage of eliminating the need for the analyst to handle solutions of the free intercalator which in some cases can be potentially hazardous. A simple variation of this technique is to immobilize sample nucleic acids rather than the labeled probe and proceed in the normal fashion. This is somewhat less advantageous but is a practical assay approach.

Solution-Phase Hybridization Formats

In addition to the above described solid-phase formats, a variety of solution-phase hybridization formats can also be applied to the present invention. Such formats are characterized by the feature that the hybridization step involves soluble forms of both the sample nucleic acids and the probe. This can result in significantly faster hybridizations since the kinetics are much faster when both strands are in solution compared to when one is immobilized. Normally, subsequent to the hybridization step, the resulting hybrids are rendered immobile for purposes of detection. Such immobilization can be accomplished in a variety of ways. Conventionally it is known to selectively immobilize complexes by exposure to adsorbents such as hydroxyapatite and nitrocellulose membranes.

A particularly useful approach to immobilizing hybrids formed from a solution-phase hybridization involves the use of a probe which comprises a reactive site capable of forming a stable covalent or noncovalent bond with a reaction partner and obtaining immobilization by exposure to an immobilized form of such reaction partner. Preferably, such reactive site in the probe is a binding site such as a biotin or hapten moiety which is capable of specific noncovalent binding with a binding substance such as avidin or an antibody which serves as the reaction partner. After the hybridization step then, one can add an immobilized form of the reaction partner, e.g., binding substance, which will effectively bind an immobilize the hybrids through the reactive site on the probe.

Essentially any pair of substances can comprise the reactive site/reactive partner pair which exhibit an appropriate affinity for interacting to form a stable bond, that is a linking or coupling between the two which remains substantially intact during the subsequent assay steps, principally the separation and detection steps. The bond formed may be a covalent bond or a noncovalent interaction, the latter being preferred especially when characterized by a degree of selectivity or specificity. In the case of such preferred bond formation, the reactive site on the probe will be referred to as a binding site and the reaction partner as a binding substance with which it forms a noncovalent, commonly specific, bond or linkage. Such binding site can be present in a single stranded hybridizable portion of the probe or can be present as a result of a chemical modification of the probe. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor), or comprises rare, antigenic nucleotides or sequences (e.g., 5-bromo or 5-iododeoxyuridine, Z-DNA) which are bindable by specific antibodies (see British Patent Specification No. 2,125,964). Binding sites introduced by chemical modification of the probe are particuarly useful and normally involve linking one member of a specific binding pair to the probe nucleic acid. Useful binding pairs from which to choose include biotin/avidin, haptens and antigens/antibodies, carbohydrates/lectins, enzymes/inhibitors, and the like. Where the binding pair consists of a proteinaceous member and a nonproteinaceous member, it will be preferred to link the nonproteinaceous member to the probe since the proteinaceous member may be unstable under the denaturing conditions of hybridization of the probe. Preferable systems involve linking the probe with biotin or a hapten and employing immobilized avidin or anti-hapten antibody, respectively. Preparation of useful ligand-labeled probes is known in the literature (Langer et al. *Proc. Natl. Acad. Sci.*, 78, 6633 (1981); Broker, *Nucl. Acids Res.*, 5, 363 (1978); Sodja et al, *Nucl. Acids Res.*, 5, 385 (1978); Tchen et al, *Proc. Natl. Acad. Sci.*, 81, 3466 (1984)). Immobilization of the binding substance can follow conventional techniques.

A large variety of methods are known for immobilizing proteins on solid supports and these methods are applicable to the immobilization of the binding substance (see *Methods in Enzymology*, Vol. 44 (1976)). Antibodies, for example, are immobilized either by covalent coupling or by noncovalent adsorption. Noncovalent methods frequently employed are adsorption to polystyrene beads or microparticles and to polyvinylchloride surface. Many covalent methods are used for immobilizing proteins and a few include cyanogen bromide activated agaroses and dextrans; glutaraldehyde activated nylons and polyacrylamides; and epoxides on acrylic and other supports.

When the probe is presented for hybridization with the sequence of interest in an immobilizable form, the subsequent steps of immobilization of the formed duplexes through a property of the probe and addition of the anti-hybrid reagent can proceed in any desired order. Immobilization and anti-hybrid addition can be accomplished by simultaneous addition of the involved reagents and materials, or one can precede the other, with or without intervening wash or separation steps, in either order. Where ordered additions are followed, of course one will take into account the concentrations of the added reagents so as not to oversaturate the formed hybrids and inhibit interaction therewith of the second added materials.

Although immobilized probes or immobilizable probes which become bound to solid supports by specific binding processes described above are preferred, immobilizable probes can be bound to supports by processes with relatively low specificity. In this case the support would bind the hybridized probe but not the unhybridized form. Then the amount of hybrid would be measured with the antibody reagent. An example of a support of this type is hydroxyapitite which binds DNA.RNA and RNA.RNA duplexes but not the single stranded species (Brenner and Falkow, *Adv. in Genet.*, 16, 81 (1973)).

Also, a chemically active or activatable group can be introduced into the probe and allowed to react with the solid support following the hybridization. This system would give a covalently immobilized probe and the amount of hybrid coupled to the support can be determined with the antibody.

In addition to the above methods, solution-phase hybridization formats can be performed wherein the hybrids are immobilized by binding of immobilized or immobilizable anti-hybrids antibody reagents. Such antibody reagents can be specific for intercalated duplexes or for DNA/RNA, RNA/RNA or DNA/DNA hybrids as described herein. Researching immobilized duplexes are detected by using directly or indirectly labeled probe, labeled second anti-hybrid antibody, or a labeled second probe.

Anti-Hybrid Antibody Reagent and Detection Schemes

The antibody reagent used in the preferred embodiments of the present invention is principally characterized by its ability to bind the hybrids formed between the probe and complementary sample nucleic acids to the significant exclusion of single stranded polynucleotides. The antibody reagent can consist of whole antibodies, antibody fragments, polyfunctional antibody aggregates, or in general any substance comprising one or more specific binding sites from an anti-hybrid antibody. When in the form of whole antibody, it can belong to any of the classes and subclasses of known immunoglobulins, e.g., IgG, IgM, and so forth. Any fragment of any such antibody which retains specific binding affinity for the hybridized probe can also be employed, for instance, the fragments of IgG conventionally known as Fab, F(ab'), and F(ab')$_2$. In addition, aggregates, polymers, derivatives and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

Useful anti-hybrid antibodies include those selective for intercalated nucleic acid duplexes as well as those which bind DNA/RNA, RNA,RNA, or DNA/RNA hybrids specifically.

Antibodies to intercalated duplexes are raised against an immunogen which usually comprise an ionic complex between a anionic protein or protein derivative (e.g., methylated bovine serum albumin) and the anionic intercalated duplexes. Preferably, the intercalation is covalently linked to the duplex. Alternatively, the intercalator duplex complex can be covalently coupled to a carrier protein.

The preparation of antibodies to DNA/DNA is described in European Patent Publication No. 135,139.

Immunogens for stimulating antibodies specific for DNA·RNA hybrids can comprise homopolymeric or heteropolymeric polynucleotide duplexes. Among the possible homopolymer duplexes, particularly preferred is poly(rA).poly(dT) (Kitagawa and Stollar, *Mol.*

*Immunol.*, 19, 413 (1982)). However, in general, heteropolymer duplexes will be preferably used and can be prepared in a variety of ways, including transcription of φX174 virion DNA with RNA polymerase (Nakazato, *Biochem.*, 19, 2835 (1980)). The selected RNA.DNA duplexes are absorbed to a methylated protein, or otherwise linked to a conventional immunogenic carrier material, such as bovine serum albumin, and injected into the desired host animal (see Stollar, *Meth. Enzymol.*, 70, 70 (1980)).

Antibodies to RNA·DNA duplexes can be raised against double stranded RNAs from viruses such as reovirus of Fiji disease virus which infects sugar cane, among others. Also, homopolymer duplexes such as poly(rI).poly(rC) or poly(rA).poly(rU), among others, can be used for immunization as above.

When the antibody reagent is used to detect hybrids, it will usually be labeled with the chemiluminescence label by suitable synthetic means.

Alternatively, the antibody reagent can be detected based on a native property such as its own antigenicity. A chemiluminescence labeled anti-(antibody) antibody or protein A will bind to the primary antibody reagent where the label for the second antibody or protein A is a conventional label as above. Further, antibody can be detected by complement fixation or the use of labeled protein A, as well as other techniques known in the art for detecting antibodies.

Where the antibody reagent is labeled, as is preferred, the labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the art and any convenient method can be used in the present invention.

Emitted light can be detected by convention means, such as by a photomultiplier tube, the signal from which can be fed to and displayed or recorded on a recorder, oscilliscope or scalar. The light could also be quantified on a luminometer.

Depending on the type of label employed, the assay may be either heterogeneous or homogeneous. In the former case complex fluids such as serum may be analyzed, however, in the latter case, a preliminary extraction or purification step may be necessary.

Typical heterogeneous and homogeneous luminescent or luminometric immunoassays are outlined below:

1. Heterogeneous Luminescent of Luminometric Immunoassay

In this type of immunoassay the substance to be assayed is reated with an antibody thereto. The free antibody is then separated from the bound antibody. The reaction is quantified by labelling either the antibody, the substance to be assayed or another molecule which can react with the free or bound moieties after separation.

2. Competitive Heterogeneous Luminescent Immunoassay

In this case an unknown amount of the substance to be assayed is mixed with a known amount of said substance coupled with a label and a known, but limited, amount of an antibody thereto. A competitive reaction between the labelled and unlabelled substance for the antibody ensues. The complexes between antibody and unlabelled substance and between antibody and labelled substance are separated from the free labelled and unlabelled substance.

The amount of labelled substance bound to antibody is related to the amount of unlabelled substance in the solution being assayed. These quantities may be determined either by measuring the amount of label bound to antibody or by measuring the amount of free labelled substance remaining. Examples of this type of assay wherein peroxidase is the label and the antibody is bound to a solid phase, via the walls of a glass test tube, are given in UK 2,044,927A.

3. Two-Site Heterogeneous Luminometric Immunoassay

In this type of immunoassay the substance to be assayed is first bound to an unlabelled antibody thereto which in turn is bound to a solid phase support, such as plastic. The complex (between antibody and substance) is then treated with a labelled antibody.

Analysis for the labelled antibody in the solid complex obtained may then be affected by separating the solid complex from the solution, and then determining either the amount of label present in the separated solid complex or the amount of label present in the residual labelled antibody dissolved in the solution.

In alternative embodiments of this type of immunoassay the substance to be assayed may either be bound consecutively to the labelled antibody and to the unlabelled, solid supported antibody or be bound to both the labelled and unlabelled antibody in one binding step.

4. Homogeneous Luminescent or Luminometric Immunoassay

This is applicable to immunoassays wherein the label is an amino or a substituted amino derivative of a 2,3-dihydro-1,4-phthalazinedione. It depends upon the light emitted from the free labelled substance of interest (or antibody thereto) being of a different intensity or wavelength to the light emitted from the bound labelled substance of interest (or antibody thereto).

In all of the above immunoassays the quantifying, detecting or locating step may be the luminescent reaction of the present invention.

The antibodies employed in the above immunoassays may be purchased commercially or prepared by known immunological techniques. The antibodies may be in the form of a complex mixture of antibodies or they may be one or more monoclonal antibodies. Only a small volume of antibody is generally required and it is maintained at the conditions of pH, ionic strength and temperature appropriate for its activity.

Antibodies to the following non-exhaustive list of substances may be usefully employed in immunoassays utilizing the present luminescent reaction: proteins such as insulin, alphafetoprotein and ferritin, hormones such as growth hormone, parathyroid hormone, follicle stimulating hormone, luteinising hormone, tyroid stimulating hormone, adrenocorticotrophic hormone, glucagon, prolactin and calcitonin, haptens/steroids such as estriol, progesterone and cortisol, drugs such as digoxiin, antigens such as cell surface antigens and carcino embryonic antigen and antibodies such as mumps virus antibody, human immunoglobulin G (IgG), rabbit IgG, sheep IgG, guinea pig IgG, donkey IgG and human immunoglobulins E and M.

The figure depicts a chemiluminescence device in accordance with the present invention. Device 10 has two compartments 12 and 14 separated by a valve means or membrane 16. Compartments 12 and 14 each contain one, but not all of the chemiluminescence reactants, i.e., chemiluminescence precursor, oxidant and enzyme. A buffered amine is contained in one or both of compartments 12 and 14. A typical vessel would, for example, contain a chemiluminescence precursor in compartment 12 and an oxidant, enzyme and buffered amine in compartment 14. A valve means 16 would control the gravity flow of chemiluminescence precursor from compartment 12 into compartment 14. Light is emitted when the flow begins. To stop the emittance of light, the valve means would be closed to stop the flow of chemiluminescence precursor.

The invention will now be described with reference to the following non-limiting examples.

EXAMPLES

Example 1

Preparation of Ligand-Bound Probe DNA

Although the method below is illustrated with a specific nucleic acid it can be used for any DNA probe. There are other various methods of labeling (nick translation, for example) nucleic acid probes known in the literature. A general method for labelling nucleic acids, hence a test sample is described below:

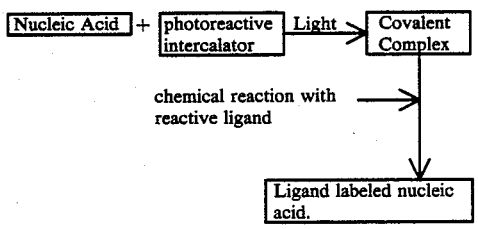

In the above, the following were employed:
(a) an ADENOVIRUS DNA or pBR322 probe (commercially available plasmid DNA probe from ENZO Biochem, New York and BRL-Bethesda Research Laboratory. Maryland).
(b) the photoreactive intercalator was an aminomethyl angelicin
(c) the reactive ligand was N-hydroxysuccinimido biotin.

The probe was first photochemically reacted with an intercalator. The intercalator was then reacted with a reactive residue of biotin. The order can be changed so that biotin residues are reacted first with a photoreactive intercalator then the product can be photochemically reacted with the probe.

A 50 μg DNA probe was dissolved in 0.500 ml borate buffer (10 mn pH 8.2) and to the solution 5 μl (5 μg) aminomethyl angelicin (1 mg/ml in $H_2O$) was added. The solution was irradiated at 346 nm for 30 minutes. The reacted nucleic acid was purified by precipitation with ethanol. The —$NH_2$ residue of the bound angelicin was reactive and could be modified with N-hydroxysuccinimide derivative of biotin (NHS biotin). This was done by dissolving aminomethyl-angelicin coupled nucleic acids (1 mg/ml) in borate buffer (10 mM pH 8.2) and adding 10 times molar excess of NHS biotin (dissolved in DMF 10 mg/ml). The mixture was shaken for 8 hours at room temperature. The resulting biotinylated DNA was purified by dialysis against phosphate buffer (10 mM $NaH_2PO_4$, 10 mM $Na_2HPO_4$, 1 mM EDTA pH 7.5). The resulting biotinylated probe was ready for hybridization.

Example 2

Dot-Blot Assay for DNA 100 ng to 1 pg photochemically biotinylated DNA were spotted on BioRad (Richmond, Calif., U.S.A.) nitrocellulose paper, baked in an oven at 80° C. for 2 hours; saturated with BSA (bovine serum albumin) by immersing the paper in 3% BSA at 42° C. for 20 minutes. Excess BSA was removed by taking the paper out of the container and blotting it between two pieces of filler papers. The paper was then incubated in a solution containing Streptavidin (0.25 mg/ml, 3.0 ml total volume), for 20 minutes at room temperature. It was then washed three times with a buffer containing Tris 0.1M, pH 7.5 0.1M NaCl, 2 mm $MgCl_2$ and 0.05% Triton X. It was incubated with biotinylated horseradish peroxidase (0.10 mg/ml) for 15 minutes at room temperature. This was followed by three washings with Tris (0.1M, pH 7.5), 0.1M NaCl, 2 mM $MgCl_2$ and 0.05% Triton X-100. The spots were punched out and the discs containing the DNA were placed in microtiter plate wells which were painted black on the sides. After the punched paper circles were placed in the microtiter plate wells 0.8 ml buffer containing 40 mM tris and 40 mM ammonium acetate (pH 8.1) was added to each well. Then 10 μl of 1:1 (v/v) mixture of 39 mM luminol in DMF and 30 mM $H_2O_2$ in water was added and a photograph of emitted light was taken. After the light decayed more $H_2O_2$+ luminol mixture was added. The reaction was continued for three days with approximately 50% loss of enzyme activity.

Example 3

Hybridization of Biotinylated Probe and Detection by Chemiluminescent Reaction

Solutions:
A. Tris-HCL buffer (1M; pH 7.5)
B. 0.5M NaOH solution
C. Tris-HCl (0.5M; pH 7.5)
D. 3 Molar NaCl
E. SSC X 20:
    175 g NaCl
    88 g Na-Citrate
    water to make 1 liter
    pH adjusted to 7.0 with HCl
    This was diluted with water to produce different SSC concentrations
F. Prehybridization Solution:
    45% formamide
    50 mm Na-phosphate buffer pH 6.5
    5×SSC
    5× Denhardts solution
    200 μg/ml single-stranded DNA in water
G. Hybridization Solution:
    45% formamide
    20 mm Na-phosphate buffer pH 6.5
    5×SSC
    5× Denhardts solution
    100 μg/ml single-stranded DNA in water.
Method:
1 μg to 1 pg of test sample DNA and control DNA (should not hybridize with the probe) were spotted onto nitrocellulose paper. The DNA samples were denatured by contacting the paper with a 3MM Whatman cellulose paper (which was soaked in and saturated with 0.5M NaOH) for 7 minutes. Then the nitrocellulose paper was brought in contact with another wet 3MM paper (which was soaked in Solution A for neutralization). The paper was dried after 2 minutes. The neutralization and drying under vacuum was repeated three times.

The nitrocellulose paper containing the immobilized denatured DNA was then contacted with a 3MM paper soaked in and saturated with solutions C and D for 5 minutes. The paper was then baked at 80° C. under vacuum for two hours. The filter was then placed in a plastic bag containing 10 mls of Solution F. The bag was incubated at 42° C. for 2 hours in a water bath. After prehybridization, the paper was taken out and placed in another bag containing 10 mls of solution G and lug labeled denatured probe (product of Example 1). Hybridization was conducted at 42° C. for 16 hours.

The nitrocellulose paper was then washed sequentially as follows:

a. with 250 ml 1×SSC +0.1% SDS: 2 washes, 3 minutes at room temperature.
b. with 250 ml 0.2SSC +0.1% SDS: 2 washes, 3 minutes at room temperature.
c. with 250 ml 0.16×SSC +0.1% SDS: 2 washes, 15 minutes at 50° C.
d. with 50 ml 2×SSC +0.1% SDS: 1 wash, 1 minute at room temperature.

The hybrids were then detected by a chemiluminescent reaction as follows: The filter with the hybrids were saturated with BSA (bovine serum albumin) by immersing the paper in 3% BSA at 42° C. for 20 minutes. Excess BSA was removed by taking the paper out of the container and blotting it between two pieces of filter paper. The paper was incubated in a solution containing Streptavidin (0.25 mg/ml, 3.0 ml total volume), for 20 minutes at room temperature. It was then washed three times with a buffer containing Tris 0.1M, pH 7.5 0.1M NaCl, 2 mm $MgCl_2$ and 0.05% Triton X. Next the filter was incubated with biotinylated horseradish peroxidase (0.10 mg/ml) for 15 minutes at room temperature. This was followed by three washings with Tris (0.1M, pH 7.5), 0.1M NaCl, 2 mM $MgCl_2$ and 0.05% Triton X-100 and one washing with 10 mM Tris (pH 8.0) buffer. Spots were punched out and the discs containing the DNA were placed in a microtiter plate with wells which were painted black on the sides. After the punched paper circles were placed in the microtiter plate wells, 0.8 ml buffer containing 40 mM Tris and 40 mM ammonium acetate (pH 8.1) was added to each well. Then 10 μl of a 1:1 mixture of 39 mM Luminol (in DMF) and 30 mM $H_2O_2$ (in water) was added. Light emission was recorded on "POLAROID" instant film by exposing it directly in the film holder.

In a dark room the light emitting papers were brought in contact with each other. The wet paper was wrapped with transparent plastic paper, e.g., "SARAN WRAP", and put directly on the open film (cover pulled using a film holder). After they were exposed, the cover was replaced and the film was developed and processed by pulling it out.

Example 4

Preparation of Enzyme-Labeled Probe and Chemiluminescent Detection of Nucleic Acid Hybrid As has been described by Renz et al *Nucleic Acids Res.*, 12, 3435 (1984), a nucleic acid probe is chemically linked to horseradish peroxidase and is hybridized to the immobilized test sample (Example 3). The method and conditions of hybridization are identical to the published precedure in *NAR.*, 12, 3435 (1984). After the hybridization the paper is washed with Tris buffer (10 mM, pH. 8), spots are punched out and are detected as described in Example 3. No post-hybridization BSA blocking is necessary when an enzyme-labeled probe is used.

Example 5

Preparation of Photoreactive Isoluminol Derivative and Hybridization

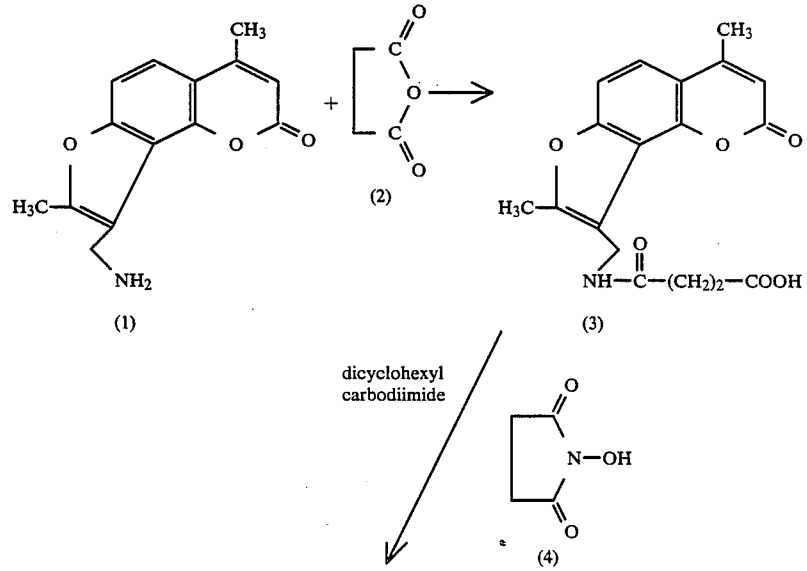

Scheme:

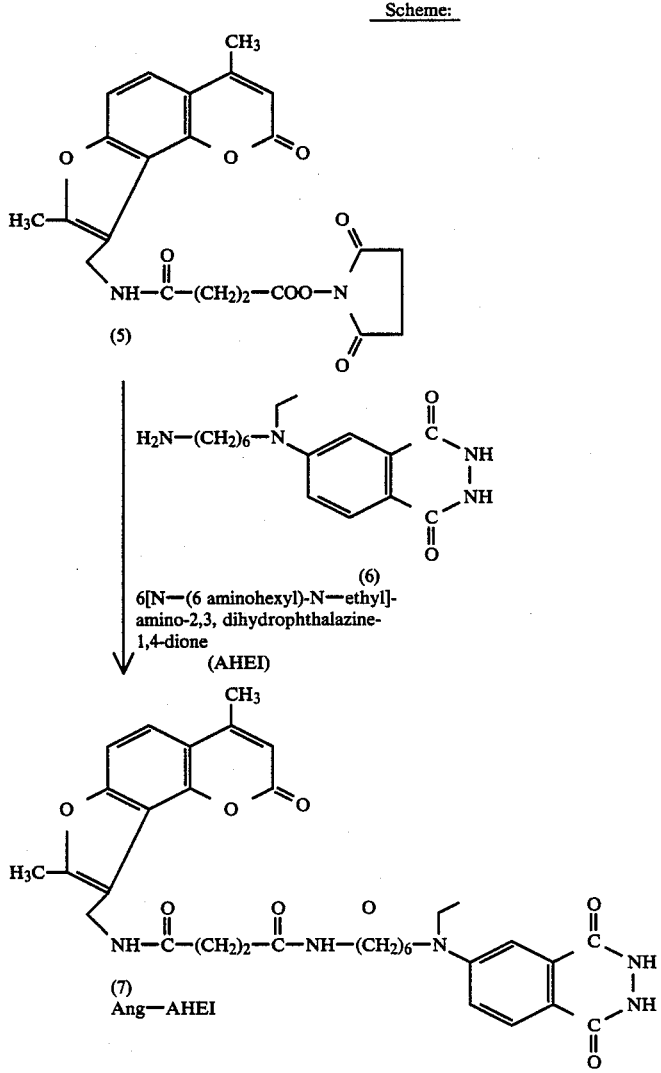

100 mg of 4'aminomethyl-4,5'-dimethylangelicin (1) and 0.4 gm of succinic anhydride are shaken together in anhydrous pyridine (5 ml) for 24 hours. Pyridine is evaporated, the residue is treated with methanol and the product is evaporated to a gummy mass. The solid is placed in 10 ml dimethyl-formamide (DMF) and 0.2 gm of dicyclohexyl carbodiimide and 0.4 gm of N-hydroxysuccinimide are added. The reaction is carried out for 24 hours. The reaction mixture is cooled to $-20°$ C. to precipitate dicyclohexylurea, which is removed by centrifugation. The resulting product is reacted with three times molar excess of AHEI (6) in DMF. The reaction is conducted by incubating the mixture for 12 hours at room temperature. DMF is then evaporated under reduced pressure. The resulting solid can be used without purification. The solid is dissolved in 10 ml DMA and 1.0 μl of this solution is added to 1 ml probe (50 μg) to be labeled and photoirradiation conducted as in Example 1, then is hybridized as in Example 3.

After hybridization, the spots are separately placed in microtiter plate wells. 1 μl (0.1 mg/ml) horseradish peroxidase, 1 ml Tris-ammonium buffer (40 mM Tris+40 mM ammonium) and 0.5 ml, 5 mM $H_2O_2$ are added. Light emission is recorded by exposuring "PO-LAROID" film.

Example 6

Oligonucleotide Detection After Hybridization

This example is divided into four parts.
6a. Synthesis of an amine containing oligionucleotide.
6b. Reaction of 6a product with N-hydroxysuccinimido biotin
6c. Purification of 6b product.
6d. Hybridization and detection of oligonucleotide by chemiluminescence.

Example 6a
Synthesis of a Reactive Amine-containing Oligonucleotide

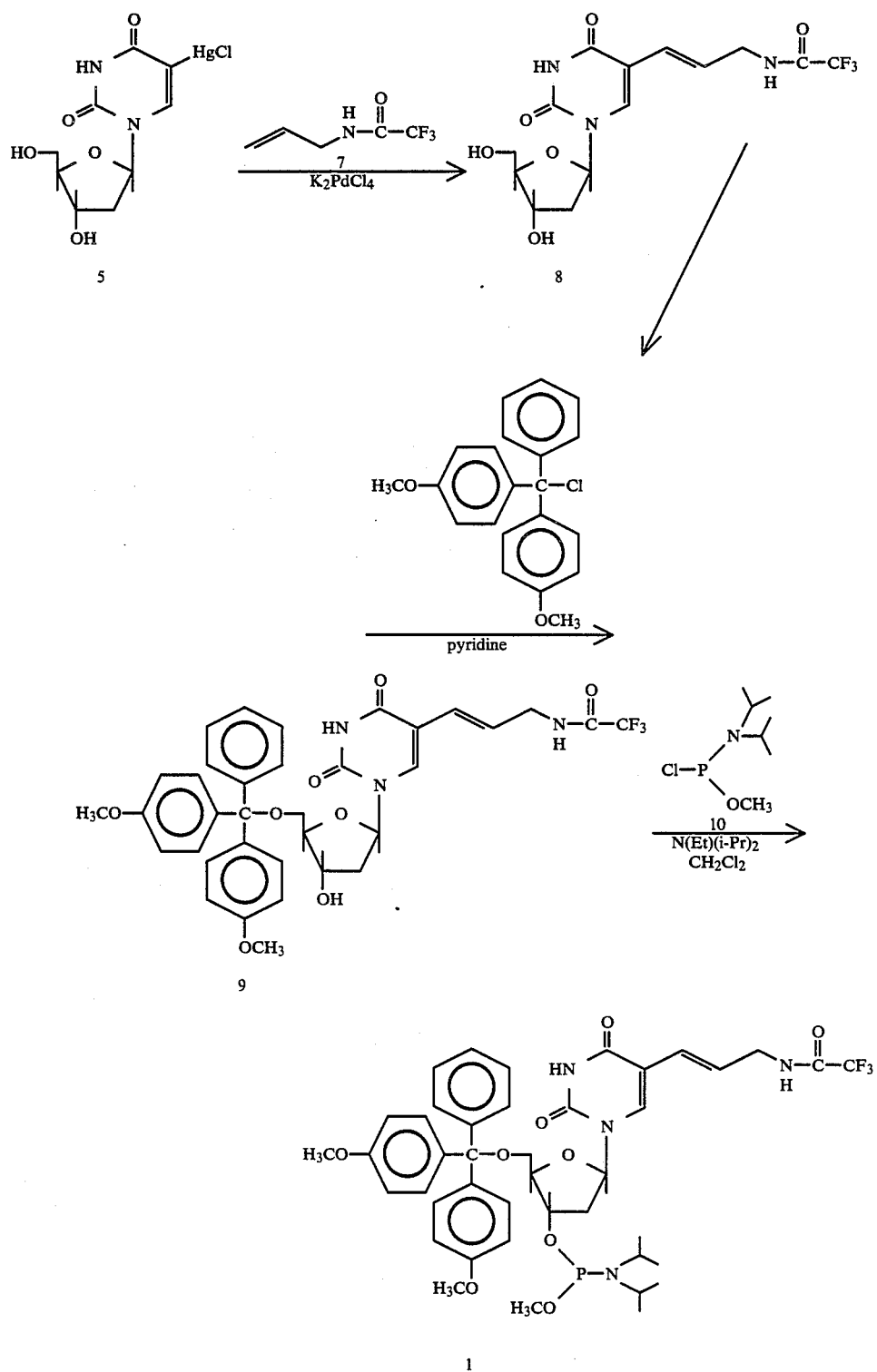

Scheme for the synthesis of 1 to be added to 19A' at the 5' end.

The synthesis of 1 is outlined in the above scheme. 5-Chloromercuri-2'-deoxyuridine (5), prepared according to the method of D. E. Berstrom and J. L. Ruth, *J. Carbohydrates, Nucleosids, and Nucleotides*, 4, 257 (1977), was treated with 3-trifluroacetamido-1-propene (7) (M. Paileand, W. J. Hubsch, *Monatshefte fur Chemie*, 97, 99 (1966)) and $K_2PdCl_4$ in methanol to give 5-trifluoroacetamidoallyl-2'deoxyuridine (8) in 22% yield after two chromatographies and a crystllization from methanol. Reaction of 8 with 4,4'-dimethoxytrityl chloride in pyridine produced 9 in 85% yield after flash chromatograph (W. C. Still, M. Kahn, A. Mitra, *J. Org. Chem.*, 43, 2923 (1978), which was subsequently treated with N,N-diisopropylaminomethoxy chlorophosphine (L. J. McBride and M. H. Caruthers, *Tet. Letters*, 24, 245 (1983)) (10) to give 1 as a white solid after precipitation from pentane. 19-unit oligonucleotides HB19A':

3'-GA-GGA-CXC-CTC-TTC-AGA-CG-5' was prepared using a DNA synthesizer. Three separate 1 μmole batches of each oligonucleotide were made and each was attached to a solid support and fully protected by a dimethoxytrityl radical. The dimethoxytrityl protecting group was removed from the 5'-terminus and 1 was attached to the 19-unit chain without the DNA synthesizer, but using the same reagents and conditions the machine (synthesizer) typically employs.

The product of this process, after removal from the support, is an oligonucleotide with a 5'-(-aminoallyl-5'-(4,4'-dimethoxytrityl)-2'-deoxy-uridine unit at the C-5' end, viz.,

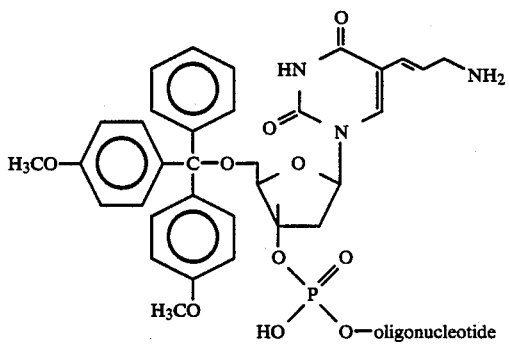

The product polynucleotides were lastly de-tritylated with brief exposure to a 3% trichloracetic acid then purified by polyacrylamide gel electrophoresis.

The polynucleotide HB19A' is a unit polynucleotide corresponding to a portion of human DNA which codes for the polypeptide beta hemoglobin, specifically that region of the DNA wherein lies the mutation which manifests itself in the formation of sickle-cell hemoglobin and the genetic disorder known as sickle cell anemia.

Infrared (IR) spectra were obtained as solutions in $CHCl_3$ unless otherwise noted. The 1602 $cm^{-1}$ band of polystyrene film was used as an external calibration standard.

Proton magnetic resonance ($^1H$ NMR) spectra were obtained in $CDCl_3$ solution unless otherwise noted. Chemical shifts are reported in parts per million downfield from the internal standard tetramethylsilane, unless otherwise noted.

Carbon-13 magnetic resonance ($^{13}C$ NMR) spectra were obtained in $CDCl_3$ solution unless otherwise noted. Carbon shifts are reported in parts per million downfield from the internal standard tetramethylsilane, unless otherwise noted.

Phosphorous-31 magnetic resonance ($^{31}PNMR$) spectra were obtained in $CDCl_3$ solution unless otherwise noted. Phosphorous shifts are reported in parts per million downfield from an external aqueous 15% $H_3PO_4$ standard.

Thin layer chromatograph (TLC) was performed using silica gel 60F-254 plates from E. Merck. Column chromatography was performed using E. Merck Silica Gel 60 (70-230 mesh).

5-Trifluoroacetamidoallyl-2'deoxyuridine (8)

A suspension of 5-chloromercuri-2'-deoxyuridine (5) (Bergstrom and Ruth, supra) (5.56 g; 12 nmol) in HPLC (high performance liquid chromatography) grade methanol (120 ml) was maintained under an inert gas atmosphere at ambient temperature and treated with 3-trifluoro-acetamido-1-propene (7) (Pailer and Hubsch, supra) (7.33 g; 48 mmol; 4 equivalents), and $K_2PdCl_4$ (4.28 g; 1.1 equivalents). The reaction gradually became black and was stirred for 22 hours. The mixture was treated with $H_2S$ gas for several minutes, then filtered through Celite, rinsed with methanol and evaporated to dryness under reduced pressure from a 80° C. bath to give a crude semi-solid residue (7.0 g). The residue was chromatographed on a silica gel column developed with $CH_2Cl_2$:MeOH (5:1). The band which stained a blue color with modified p-anisaldehyde reagent (Egon Stahl, *Thin Layer Chromatograph*, 2nd Edition, Springer-Verlong, N.Y., 857 (1969)) and had an $R_f=0.51$ ($CH_3CN$:MeOH 3:1) was collected and evaporated to dryness in vacuo to give a colorless form. The product was crystallized from a minimum of methanol, filtered, washed with cold $CHCl_3$:MeOH (3:1) and vacuum dried. The mother liquor was worked for a second crop-total yield 1.01 g (22%). A recrystallization from MeOH produced the title compound (8) as analytically pure tiny white needles with mp=183°-4° after drying in vacuo (<1.0 torr) at 64° C. overnight. IR(KBr) $cm^{-1}$ 3420, 3260, 1718, 1683 (br), 1560, 1478, 1283, 1190, 1102, 1061, 980, 788, 763, 737; $^1HNMR$ (DMSO-$d^6$) (Ref. DMSO-$d^6$) 2.13 (d of d, J=6 Hz, 2H), 3.59 (br s, 2H), 3.70–3.97 (m, 3H), 4.25 (br s, 1H), 5.06 (br, m, 1H), 5.20 (br m, 1H), 6.05–6.65 ($m_6$, 4H), 8.01 (s, 1H), 9.60 (br s, 1H); $^{13}NMR$ (DMSO-$d^6$) (Ref. DMSO-d) ppm 162.05, 155.29, 149.50, 138.05, 124.33, 124.14, 109.96, 87.53, 84.47, 70.23, 61.12, 39.93; $(\alpha)_D=+8.01°$ (c=0.87, MeOH).

Anal. Calculated for $C_{14}H_{16}N_3O_6F_3$: C, 44.33; H, 4.25; N, 11.08. Found: C, 44.19; H, 4.10; N, 10.93

5-Trifluoroacetamidoallyl-5'-O-(4,4'-dimethoxytrityl)-2'deoxyuridine (9)

A solution of 8 (0.60 g; 1.58 mmol) in anhydrous pyridine (8 ml) was maintained under an inert gas atmosphere and treated at ambient temperature with 4,4'-dimethoxytrityl chloride (0.67 g; 1.25 equivalents). After stirring for 18 hours, the reaction was poured into ice water (70 ml) with vigorous shaking. On standing one-third of an hour at 0° C., a gummy solid was separated out, leaving a nearly clear solution which was decanted. The solid was washed once with $H_2O$ (5 ml), then taken up in $CH_3Cl_2$ (10 ml), washed once with brine (5 ml), then the $CH_2Cl_2$ solution was dried over $K_2CO_3$, filtered and evaporated to dryness in vacuo to give a brownish foam. The crude product was purified by flash chromatography (Still et al, supra) on a column of silica gel (Merck, Grade 60, 230–400 mesh, 60A) (75 g) developed with 4.0% MeOH in $CHCl_3$ solvent (1.0 L). Fractions of ca. 20 ml each were collected in tubes containing pyridine (10 μl) to inhibit deprotection of the 5'hydroxyl. Fractions. containing the major product band (Rf=0.29; MeOH: $CHCl_3$ 7.93) were combined, filtered and evaporated to dryness in vacuo to give 9 (0.91 g; 85%) as a slightly yellowish foam. A fraction from the center of the elution band was freed of solvent, taken upin ethylacetate (EtoAc), treated with "NORIT 211" (sold by General Norit Co.), filtered through "CELITE" (an analytical filter aid-sold by chem Alert) and evaporated to dryness under high vacuum (<1.0 torr) at 64° C. overnight to afford the analytical sample as a colorless foam with mp=105°-110° C. (dec.). IR (CHCl$_3$)cm$^{-1}$ 3370, 2920, 1715, 1695, 1618, 1515, 1470, 1260, 1182, 1045, 842; $^1$H NMR (CDCl$_3$) $\gamma$2.38 (br m, 2H) 3.25-3.75 (m, 5H), 3.75 (s, 6H), 4.10 (br m, 1H), 4.60 (br s, 1H), 5.39 (d, J=16 Hz, 1H), 6.10-6.55 (m, 2H), 6.70-6.95 (m, 5H, 7.15-7.45 (m, 10H), 7.84 (s, 1H); $^{13}$C NMR (CDCl$_3$) Ref. CDCl$_3$) ppm 162.31, 158.74, 157.70, 156.01, 149.70, 144.04, 137.88, 135.65, 135.52, 130.12, 128.11, 127.26, 125.05, 113.48, 111.33, 86.94, 86.68, 85.25, 72.18, 63.60, 55.34, 42.66, 41.42.

Anal. Calculated for $C_{35}H_{34}N_3O_8F_3$: C, 61.67; H, 5.03; N, 6.16.

Found: C, 61.47; H, 5.19; N, 5.95

5-Trifluoroacetamidoallyl-5'0-(4,4'-dimethoxytrityl)-2'deoxyuridine-3'-0-(N,N-diisopropylaminomethoxy phospine) (1)

A solution of 9 (0.34 g; 0.5 mmol) in anhydrous CH$_2$Cl$_2$ (1.5 ml) maintained under an argon atmosphere at ambient temperature was treated first with anhydrous, diisopropylethylamine (0.35 ml; 0.259 g; 2 mmol; 4 equivalents) then dropwise, over 1 minute with N, N-diisopropylaminomethoxy-chlorophosphine (see McBride et al, supra) (10) (0.19 ml; ca 0.2 g; 2.2 equivalents). The resultant colorless solution was stirred for 20 minutes then transferred with EtOAc (20 ml) (EtOAC) was previously washed with saturated aqueous NaHCO$_3$, then brine to a separatory funnel, washed four times with brine (35 ml each), dried over Na$_2$SO$_4$, filtered and evaporated to dryness in vacuo to give a colorless glass (0.51 g.). This crude product was taken up in anhydrous benzene (2 ml) and precipitated into rapidly stirred anhydrous pentane (60 ml) at −78° C. under an Argon atmosphere. The resulting suspension was filtered, washed with −78° C. pentane and vacuum dried at <1 torr over KOH overnight to obtain the title compound (1) (0.38 g; 93%) as a white amorphous powder. IR (CHCl$_3$) cm$^{-1}$ 2965, 1722, 1698, 1618, 1518, 1470, 1262, 1185, 1045, 988, 842; $^1$H NMR (CD$_2$Cl$_2$) $\gamma$ 0.95-1.30 (m, 12H), 2.20-2.60 (m, 2H), 3.24 and 3.37 (d of d, J=13 Hz, 3H) (P—O—CH$_3$), 3.20-3.80 (m, 6H), 3.75 (s, 6H), 4.17 (br m, 1H), 4.68 (v br m, 1H), 5.42 (d, J=16 Hz, 1H), 6.15-6.55 (m, 3H), 6.75-6.95 (m, 4H), 7.20-7.50 (m, 10H) 7.79 (s, 1H); $^{13}$C NMR (CD$_2$Cl$_2$) (Ref. CD$_2$Cl$_2$) ppm 162.40, 159.21, 157.78, 149.78, 144.71, 138.34, 136.00, 130.53, 128.71, 128.45, 127.54, 125.66, 125.27, 113.82, 111.48, 87.23, 86.31, 85.60, 55.75, 43.78, 43.20, 42.94, 24.99, 24.60; $^{31}$PNMR (CD$_2$Cl$_2$) ppm 149.30, 148.87, 14.11 (approximately 12% impurity), 8.18 (approximately 4% impurity).

Attachment of 1 to Oligonucleotides

The 19-unit oligonucleotides were synthesized using an Applied Bio-systems Model 380A DNA Synthesizer on control pore glass solid support. Immediately prior to attaching 1 to the 5' end of the oligomer, the 5'-0-(4,4'-dimethoxytrityl) protecting group was cleaved on the machine with 3% CCl$_3$CO$_2$H in CH$_2$Cl$_2$ for 90 seconds. The support-bound 5' deprotected oligomer was washed with CH$_3$CH and dried in an argon stream. Subsequent steps were performed without the machine (synthesizer), but using the same chemistry;

1. The support-bound oligomer was removed from the container (column) used for automated synthesis and transferred to dry septum-cap vial under an argon atmosphere.
2. The bound oligomer was treated with a 20–30 fold excess of 0.5 MlH-tetrazole in anhydrous CH$_3$CN. It was incubated for 30 minutes with gentle agitation.
3. Reagents were pipetted-off and the bound oligomer was washed with three portions of CH$_3$CN.
4. The solid support containing the bound oligomer was treated with an excess of I$_2$H$_2$O-Lutidine-THF (0.1M: 1:10:40) and agitated for 15 minutes.
5. Reagents were pipetted and the bound oligomer was washed with four portions of CH$_3$CN.
6. The solid support containing the bound oligomer was washed with an excess of thiophenol-triethylamine-dioxane for 60 minutes.
7. Reagents were pipetted-off and the bound oligomer was washed with four portions of MeOH.
8. The solid support containing the bound oligomer was treated with concentrated aqueous NH$_4$OH for 2 hours at ambient temperature (this removes protected oligonucleotide from the support).
9. To remove all protecting groups, the oligonucleotide was treated with concentrated aqueous NH$_4$OH and heated at 50° C. overnight (this removes all protecting groups, except the dimethoxytrityl).
10. The support was filtered-off and the filtrate was evaporated to dryness to obtain crude oligonucleotide.

The above ten steps were repeated for all batches of support-bound oligonucleotide. Treatment of a portion of each on a silica gel TLC plate with 3% CCl$_3$CO$_2$H in CH$_2$Cl$_2$ produced the orange-red color of dimethoxytrityl cation indicating the successful incorporation of 1 into the oligonucleotides.

One bath of the modified HB19A' oligonucleotide was detritylated with 3% CCl$_3$CO$_2$H in CH$_2$Cl$_2$, and purified by electrophoresis on polyacrylamide gel.

Example 6b:

The reaction of a specific oligonucleotide with N-hydroxsuccinimido Bitoin (NHS-biotin)

Two micrograms of 19A' amine or 19S'-amine from Examples 6a were dissolved in 20 microliters of 10mM borate buffer pH 8.16. To this, 5 microliters of a freshly prepared DMF solution of N-hydroxysuccinimido biotin (10 mg/ml) purchased from Pierce were added. The reaction was allowed to proceed at room temperature for 16 hours. After the reaction, the solvent was evaporated under reduced pressure.

Example 6c:

The separation of NHS biotin reacted 19A' from the reaction mixture

HPLC separation is conducted on a Brownlee RP300 guard column coupled to a Synchropack RPP 4.1×10 cm (Synchrom; Linden, Ind.) column at ambient temperature with a gradient of 0.1M triethylammonium acetate pH 7 to 0.1M triethylammonium acetate pH 7, 50% acetonitrile is run over a period of 10–120 minutes depending on the sample. The detector is set at 254 nm and full scale is 0.15 absorbance unit. In order to determine the location of the derivatized oligonucleotide product, a blank run is carried out with the reaction mixture without the oligonucleotide. A new peak appears after adding the oligonucleotide and corresponds to the reaction product. After the product is separated and collected in a fraction collector, the product is analyzed by gel electrophoresis and from the next run an analytical determination of the proper peak is found to be not necessary. The oligonucleotide is then evaporated to dryness under reduced pressure.

Example 6d:

Hybridization and Detection of a Hybridized Oligonucleotide

For demonstration purposes purified blood DNA is immobilized on nitrocellulose paper, prehybridized as in Example 3, hybridized with biotinylated oligonucleotide product of Example 6c under conditions as described in Conner et al, *Proc. Natl. Acad. Sci., U.S.*, 80, 278 (1983) and detected by chemiluminescent method as in Example 2.

Example 7:

Examples 2, 3, 5 and 6 were repeated using other buffers instead of tris+ammonium. Such other buffers were as follows:
(i) 40 mM tris+40 mM imidazole pH 8.1
(ii) 40 mM tris+10 mM pyridine pH 8.1
(iii) 40 mM tris+10 mM spermine pH 8.1

Better results were obtained with ammonium. All these nitrogenous compounds in buffers (i), (ii), and (iii) were, however, effective in delaying the chemiluminescence emission and kept the enzyme in active form for a long period of time, thus enhancing the emission.

Example 8:

Assay for antirubella IgG:

As has been described by Thorpe et al, (*Biochem. Biophys. Res. Cem.*, 119, 481 (1984)), a Rubazyme Kit (Abbot Diagnostic) is used for this assay. Polystyrene beads are coated with Rubella virus. The test sample is then incubated with the virus coated beads in (10 mM tris (pH 7.5) buffer. The unreacted test components are removed by separating the beads and washing them.

The beads are then reacted with antihuman IgG (goat)/horseradish peroxidase (IgG-HRP) conjugate. After removing any unreacted IgG-HRP the beads are placed in microliter plate wells. Enough buffer (approximately 1 ml) 40 mM tris+40 mM ammonium acetate (pH=8.1) is added to submerge the beads. 40π 1:1 (v/v) mixture of 3 mm luminol (in DMF) and 30 mM $H_2O_2$ (in $H_2O$) were added. Light emission is monitored by exposing a "POLAROID" instant film as in Example 3.

It will be appreciated that the instant specification and claims are set forth by way of illustration and non limitation, and that various modifications and changes may be made without departure from the spirit and scope of the present invention.

What is claimed is:

1. In a process for the generation of light chemiluminescently by contacting a chemiluminescence precursor, an oxidant, and an enzyme, the improvement which comprises said chemiluminesense precursor being a 2,3-dihydro-1,4-phthalazinedione of the formula

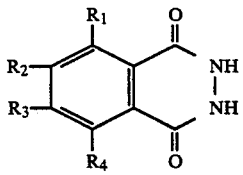

wherein $R_1$ is an amino and $R_2$, $R_3$ and $R_4$ are all H, and wherein $R_1$ is amino and each of $R_2$, $R_3$ and $R_4$ is unsubstituted or substituted $C_1$–$C_6$ alkyl, unsubstituted or substituted alkenyl, unsubstituted or substituted hydroxyl, $C_1$–$C_6$ alkoxy, carboxyl, or amino, or $R_2$ is amino and each of $R_1$, $R_3$ and $R_4$ is H, unsubstituted or substituted $C_1$–$C_6$-alkyl, unsubstituted or substituted $C_2$–$C_{10}$ alkenyl, unsubstituted or substituted hydroxyl, $C_1$–$C_6$ alkoxy, carboxyl, or amino, or $R_1$ and $R_2$ together with the ring carbons they are attached to form a fused benz ring substituted with an amino or substituted amino group, and each of $R_3$ and $R_4$ is H, unsubstituted or substituted $C_1$–$C_6$-alkyl, unsubstituted or substituted alkenyl, unsubstituted or substituted hydroxyl, $C_1$–$C_6$-alkoxy, carboxyl or amino, substituents for said substituted alkyl and alkenyl being selected from the group consisting of chlorine, flourine, bromine, iodine, hydroxy, carboxy, nitro, cyano and thiol, said substituted amino being substituted by a substituent selected from the group consisting of $C_1$ to $C_{10}$ alkyl and $C_2$ to $C_{10}$ alkenyl, said substituted hydroxy being substituted by a substituent selected from the group consisting of $C_1$ to $C_{10}$ alkyl and $C_2$ to $C_{10}$ alkenyl, said enzyme being a peroxidase enzyme and effecting such cntact in the presence of a nitrogen compound selected from the group consisting of (a) ammonia and its salts, (b) a heterocyclic aromatic, wherein said heterocyclic aromatic is selected from the group consisting of imidazoles and alkyl derivatives thereof, pyridine and alkyl derivatives thereof and thiazine, said thiazine selected from the group consisting of thionine and methylene blue, and (c) a water-soluble organic amine, said water-soluble organic amine selected from the group consisting of alkyl amines, polyamines selected from the group consisting of spermine, spermidine and putrescine, benzylamine, said alkyl amine being of the formula

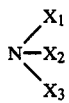

wherein $X_1$, $X_2$ and $X_3$ are the same or different and are unsubstituted alkyl having 1 to 8 carbon atoms or alkyl having 1 to 8 carbon atoms and substituted by a substituent selected from the group consisting of hydroxy, nitro, fluorine, chlorine, bromine, iodine and carboxy.

2. A chemiluminescence process according to claim 1, wherein said nitrogen compound is $NH_3$ or a salt thereof.

3. A chemiluminescence process according to claim 1, wherein the oxidant is hydrogen peroxide.

4. A chemiluminescence process according to claim 1, wherein said enzyme is selected from the group consisting of horseradish peroxidase, microperoxidase and lactoperoxidase.

5. A process according to claim 1, wherein the water-soluble organic amine is benzylamine.

6. A chemiluminescence assay for the detection of a peroxidase enzyme comprising contacting a sample suspected of containing said peroxidase enzyme with a chemiluminescence precursor, an oxidant and a nitrogen compound selected from the group consisting of ammonia and its salts, a heterocyclic aromatic and a water-soluble organic amine, determining the extend of light emission and relating the amount of light emission to the amount of enzyme in the sample, said chemiluminescence precursor being a 2,3-dihydro-1,4-phthalazinedione of the formula

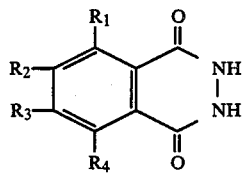

wherein $R_1$ is an amino and $R_2$, $R_3$ and $R_4$ are all H, and wherein $R_1$ is amino and each of $R_2$, $R_3$ and $R_4$ is unsubstituted or substituted $C_1$-$C_6$ alkyl or unsubstituted or substituted alkenyl, unsubstituted or substituted hydroxyl, $C_1$-$C_6$ alkoxy, carboxyl, or amino, or $R_2$ is amino and each of $R_1$, $R_3$ and $R_4$ is H, unsubstituted or substituted $C_1$-$C_6$ alkyl, unsubstituted or substituted alkenyl, unsubstituted or substituted hydroxyl, $C_1$-$C_6$ alkoxy, carboxyl or amino, or $R_1$ and $R_2$ together with the ring carbons they are attached to form a fused benz ring substituted with an amino or substituted amino group, and each of $R_3$ and $R_4$ is H, unsubstituted or substituted $C_1$-$C_6$ alkyl, unsubstituted or substituted alkenyl, unsubstituted or substituted hydroxyl, $C_1$-$C_6$ alkoxy, carboxyl or amino, said substituted alkyl and alkenyl being substituted by a substituent selected from the group consisting of chlorine, fluorine, bromine, iodine, hydroxy, carboxy, nitro, cyano and thiol, said substituted amino being substituted by a substituent selected from the group consisting of $C_1$ to $C_{10}$ alkyl and $C_2$ to $C_{10}$ alkenyl, said substituted hydroxy being substituted by a substituent selected from the group consisting of $C_1$ to $C_{10}$ alkyl and $C_2$ to $C_{10}$ alkenyl, said enzyme being a peroxidase enzyme, said water soluble organic amine selected from the group consisting of alkyl amines, polyamines selected from the group consisting of spermine, spermidine and putrescine, benzylamine, said alkyl amines are of the formula

wherein $X_1$, $X_2$, $X_3$ are the same or different and are unsubstituted alkyl having 1 to 8 carbon atoms, or alkyl having 1 to 8 carbon atoms and substituted by a substituent selected from the group consisting of hydroxy, nitro, fluorine, chlorine, bromine, iodine and carboxy and wherein said heterocyclic aromatic is selected from the group consisting of imidazoles and alkyl derivatives thereof, pyridine and alkyl derivatives thereof and thiazine, said thiazine selected from the group consisting of thionine and methylene blue.

7. A chemiluminescence immunoassay according to claim 6, wherein the water-soluble organic amine is benzylamine.

8. A test kit for the generation of chemiluminescence light comprising a chemiluminescence precursor, an enzyme, an oxidant and a nitrogen compound selected from the group consisting of ammonia and its salts, a heterocyclic aromatic and a water-soluble organic amine, said chemiluminescence precursor being a 2,3-dihydro-1,4-phthalazinedione of the formula

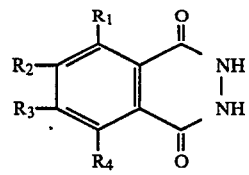

wherein $R_1$ is an amino, and $R_2$, $R_3$ and $R_4$ are all H, and wherein $R_1$ is amino and each of $R_2$, $R_3$ and $R_4$ is unsubstituted or substituted $C_1$-$C_6$ alkyl or unsubstituted or substituted alkenyl, unsubstituted or substituted hydroxyl, $C_1$-$C_6$ alkoxy, carboxyl, or amino, or $R_2$ is amino and each of $R_1$, $R_3$ and $R_4$ is H, unsubstituted or substituted $C_1$-$C_6$ alkyl, unsubstituted or substituted alkenyl, unsubstituted or substituted hydroxyl, $C_1$-$C_6$ alkoxy, carboxyl, or amino, or $R_1$ and $R_2$ are together with the rng carbons they are attached to form a fused benz ring substituted with an amino or substituted amino group, and each of $R_3$ and $R_4$ is H, unsubstituted or substituted $C_1$-$C_6$ alkyl, unsubstituted or substituted alkenyl, unsubstituted or substituted hydroxyl, $C_1$-$C_6$ alkoxy, carboxyl or amino, said substituted alkyl and alkenyl being substituted by a substituent selected from the group consisting of chlorine, fluorine, bromine, iodine, hydroxy, carboxy, nitro, cyano and thiol, said substituted amino being substituted by a substituent selected from the group consisting of $C_1$ to $C_{10}$ alkyl and $C_2$ to $C_{10}$ alkenyl, said substituted hydroxy being substituted by a substituent selected from the group consisting of $C_1$ to $C_{10}$ alkyl and $C_2$ to $C_{10}$ alkenyl, said enzyme being a peroxidase enzyme, said water soluble organic amine compound selected from the group consisting of alkyl amines, polyamines selected from the group consisting of spermine, spermidine and putrescine, benzylamine, said alkyl amines are of the formula

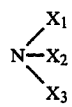

wherein $X_1$, $X_2$, $X_3$ are the same or different and are unsubstituted alkyl having 1 to 8 carbon atoms, or alkyl having 1 to 8 carbon atoms and substituted by a substituent selected from the group consisting of hydroxy, nitro, fluorine, chlorine, bromine, iodine and carboxy, and wherein said heterocyclic aromatic is selected from the group consisting of imidazoles and alkyl derivatives thereof, pyridine and alkyl derivatives thereof and thiazine, said thiazine selected from the group consisting of thionine and methylene blue.

9. A test kit according to claim 8, wherein the water-soluble organic amine is benzylamine.

10. A chemiluminescence device comprising a vessel and means for combining a nitrogen compound selected from the group consisting of ammonia and it salts, a heterocyclic aromatic, and a water-soluble organic amine, and chemiluminescence reactants including a chemiluminescence precursor, an oxidant, and an enzyme, said chemiluminescence precursor being a 2,3-dihydro-1,4-phthalazinedione of the formula

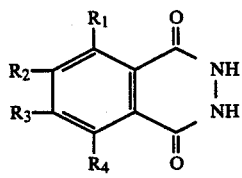

wherein $R_1$ is an amino, and $R_2$, $R_3$ and $R_4$ are all H, and wherein $R_1$ is amino and each of $R_2$, $R_3$ and $R_4$ is unsubstituted or substituted $C_1$-$C_6$ alkyl or unsubstituted or substituted alkenyl, unsubstituted or substituted hydroxyl, $C_1$-$C_6$ alkoxy, carboxyl, or amino, or $R_2$ is amino or substituted alkenyl, unsubstituted or substituted hydroxyl, $C_1$-$C_6$ alkoxy, carboxyl, or amino, or $R_2$ is amino and each of $R_1$, $R_3$ and $R_4$ is H, unsubstituted or substituted $C_1$-$C_6$ alkyl, unsubstituted or substituted alkenyl, unsubstituted or substituted hydroxyl, $C_1$-$C_6$ alkoxy, carboxyl, or amino, or $R_1$ and $R_2$ together with the ring carbons they are attached to form a fused benz ring substituted with an amino or substituted amino group, and each of $R_3$ and $R_4$ is H, unsubstituted or substituted $C_1$-$C_6$ alkyl, unsubstituted or substituted akenyl, unsubstituted or substituted hydroxyl, $C_1$-$C_6$ alkoxy, carboxyl or amino, said substituted alkyl and alkenyl being substituted by a substituent selected from the group consisting of chlorine, fluorine, bromine, iodine, hydroxy, carboxy, nitro, cyano and thiol, said substituted amino being substituted by a substituent selected from the group consisting of $C_1$ to $C_{10}$ alkyl and $C_2$ to $C_{10}$ alkenyl, said substituted hydroxy being substituted by a substituent selected from the group consisting of $C_1$ to $C_{10}$ alkyl and $C_2$ to $C_{10}$ alkenyl, said enzyme being a peroxidase enzyme, said water soluble organic compound selected from the group consisting of alkyl amines, polyamines selected from the group consisting of spermine, spermidine and putrescine, benzylamine, said alkyl amines are of the formula

wherein $X_1$, $X_2$, $X_3$ are the same or different and are unsubstituted alkyl having 1 to 8 carbon atoms, or alkyl having 1 to 8 carbon atoms and substituted by a substituent selected from the group consisting of hydroxy, nitro, fluorine, chlorine, bromine, iodine and carboxy, and wherein said heterocyclic aromatic is selected from the group consisting of imidazoles and alkyl derivatives thereof, pyridine and alkyl derivatives thereof and thiazine, said thiazine selected from the group consisting of thionine and methylene blue.

11. A chemiluminescence device according to claim 10, wherein said vessel contains at least two compartments and wherein one of said compartments contains at least one, of but not all of said chemiluminescence reactants, and another of said compartments contains at least one of but, not all of said chemiluminescence reactants, and means for allowing for the controlled flow of said reactants and said nitrogen compound from one compartment to the other.

12. A chemiluminescence device according to claim 10, wherein the water-soluble organic amine is benzylamine.

13. A process for detecting an antigen or a hapten comprising contacting in a first mixture a sample suspected of containing said antigen or said hapten with an antibody reactive with said antigen or said hapten, said antibody linked to a chemiluminescence precursor, separating out any resultant antibody-antigen or antibody-hapten complex, adding to the complex a second mixture, the second mixture comprising an oxidant, an enzyme and a nitrogen compound, determining the extent of light emission and relating the amount of light emission to the amount of antigen or hapten, wherein the precursor, the nitrogen compound and the enzyme are as defined in claim 1.

14. A process according to claim 13, wherein the oxidant is selected from the group consisting of a peroxide and a perborate ion.

15. A process for detecting an antibody comprising contacting in a first mixture a sample suspected of containing said antibody with an antigen or hapten reactive with said antibody, said antigen or hapen being linked to a chemiluminescence precursor, separating out any resultant antibody-antigen or antibody-hapten complex, adding to the complex a second mixture, the second mixture comprising an oxidant, an enzyme and a nitrogen compound, determining the extent of light emission and relating the amount of light emission to the amount of the antibody, wherein the precursor, the nitrogen compound and the enzyme are as defined in claim 1.

16. A process according to claim 15, wherein the oxidant is selected from the group consisting of a peroxide and a perborate ion.

17. A process for detecting a specific single stranded nucleic acid comprising contacting under hybridization conditions in a first mixture a sample suspected of containing said specific nucleic acid with a probe, the probe comprising a nucleic acid containing a sequence complementary to the suspected specific nucleic acid in the sample, said probe being linked to biotin, separating out any resultant hybridized material, adding to the hybridized material avidin or strepavidin linked to a chemiluminescence precursor, separating out the resultant nucleic acid-avidin-biotin complex and adding a second mixture, the second mixture comprising an oxidant, an enzyme and a nitrogen compound, determining the extent of light emission and relating the amount of light emission to the amount of nucleic acid hybrid, wherein the precursor, the nitrogen compound and the enzyme are as defined in claim 1.

18. A process for detecting a specific single stranded nucleic acid comprising contacting in a first mixture a sample suspected of containing said specific nucleic acid with a probe, the probe comprising a nucleic acid containing a sequence complementary to the suspected specific nucleic acid in the sample under hybridization conditions, said probe linked to a chemiluminescence precursor, separating out any resultant hybridized material, adding to the hybridized material a second mixture, the second mixture comprising an oxidant, an enzyme and a nitrogen compound, determining the extent of light emission and relating the amount of light emission to the amount of nucleic acid hybrid, wherein the precursor, the nitrogen compound, and the enzyme are as defined in claim 1.

19. A process according to claim 18, wherein the oxidant is selected from the group consisting of a peroxide and a perborate ion.

20. The process of claim 18 wherein said chemiluminescence precursor is linked to said probe by means of an intercalator-precursor conjugate which is photochemically linked to said probe.

* * * * *

UNITED STATES PATENT AND TRADEMARK OFFICE
CERTIFICATE OF CORRECTION

PATENT NO. : 4,853,327
DATED : Aug. 1, 1989
INVENTOR(S) : Dattagupta

It is certified that error appears in the above-identified patent and that said Letters Patent is hereby corrected as shown below:

| | |
|---|---|
| Col. 9, line 39 | Delete "of" and substitute --if-- |
| Col. 11, line 44 | Correct spelling of --temperature-- |
| Col. 13, line 24 | Insert --O.-- before "Norphillin" |
| Col. 17, line 1 | Insert --of-- after "pair" |
| Col. 17, line 68 | Correct spelling of --under vacuum-- |
| Col. 23, line 52 | Correct spelling of --reacted-- |
| Col. 27, line 27 | Delete "filter" and substitute --filters-- |
| Col. 35, line 1 | Correct spelling of --up in-- |
| Col. 37, line 53 | Delete "40 π" and substitute --40μl-- |
| Col. 38, line 34 | Correct spelling of --contact-- |
| Col. 39, line 7 | Delete "extend" and substitute --extent-- |
| Col. 40, line 26 | Delete "rng" and substitute --ring-- |
| Col. 41, line 27 | Correct spelling of --alkenyl-- |

Signed and Sealed this

Twenty-second Day of January, 1991

*Attest:*

HARRY F. MANBECK, JR.

*Attesting Officer*  *Commissioner of Patents and Trademarks*